(12) United States Patent
Mitani et al.

(10) Patent No.: US 8,206,902 B2
(45) Date of Patent: Jun. 26, 2012

(54) METHOD OF AMPLIFYING NUCLEIC ACID AND METHOD OF DETECTING MUTATED NUCLEIC ACID USING THE SAME

(75) Inventors: Yasumasa Mitani, Aki-Takata (JP);
Takanori Oka, Aki-Takata (JP);
Yoshihide Hayashizaki, Tsukuba (JP);
Toshizo Hayashi, Tsurumi-ku (JP)

(73) Assignees: Riken, Saitama (JP); Kabushiki Kaisha Dnaform, Kanagawa (JP)

( * ) Notice: Subject to any disclaimer, the term of this patent is extended or adjusted under 35 U.S.C. 154(b) by 551 days.

(21) Appl. No.: 10/583,706

(22) PCT Filed: Dec. 24, 2004

(86) PCT No.: PCT/JP2004/019346
§ 371 (c)(1),
(2), (4) Date: Apr. 12, 2007

(87) PCT Pub. No.: WO2005/063977
PCT Pub. Date: Jul. 14, 2005

(65) Prior Publication Data
US 2007/0190531 A1    Aug. 16, 2007

(30) Foreign Application Priority Data

Dec. 25, 2003  (JP) ................................. 2003-431003
Oct. 28, 2004  (JP) ................................. 2004-313910

(51) Int. Cl.
*C12Q 1/68* (2006.01)
*C07H 21/04* (2006.01)
*C12P 19/34* (2006.01)

(52) U.S. Cl. ........................ 435/6.1; 435/91.2; 536/24.3

(58) Field of Classification Search ........................ None
See application file for complete search history.

(56) References Cited

U.S. PATENT DOCUMENTS 4,672,040 A    6/1987    Josephson
(Continued)

FOREIGN PATENT DOCUMENTS

EP    0 320 308    6/1989
(Continued)

OTHER PUBLICATIONS

Nollau et al. (Clinical Chemistry, 1997, 43(7):1114-1128).*
(Continued)

*Primary Examiner* — Stephanie K Mummert
(74) *Attorney, Agent, or Firm* — Hamre, Schumann, Mueller & Larson, P.C.

(57) ABSTRACT

A primer set that allows a target nucleic acid to be amplified specifically and efficiently. The primer set of the present invention includes at least two primers that allow a target nucleic acid sequence to be amplified. A first primer included in the primer set contains, in its 3' end portion, a sequence (Ac') that hybridizes to a sequence (A) located in the 3' end portion of the target nucleic acid sequence. The first primer also contains, on the 5' side of the sequence (Ac'), a sequence (B') that hybridizes to a complementary sequence (Bc) to a sequence (B) that is present on the 5' side with respect to the sequence (A) in the target nucleic acid sequence. A second primer included in the primer set contains, in its 3' end portion, a sequence (Cc') that hybridizes to a sequence (C) located in the 3' end portion of a complementary sequence to the target nucleic acid sequence. The second primer also contains, on the 5' side of the sequence (Cc'), a folded sequence (D-Dc') that contains, on the same strand, two nucleic acid sequences that hybridize to each other.

7 Claims, 16 Drawing Sheets

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 4,849,336 | A | 7/1989 | Miyoshi et al. |
| 5,314,809 | A | 5/1994 | Erlich et al. |
| 5,468,613 | A | 11/1995 | Erlich et al. |
| 5,512,439 | A | 4/1996 | Hornes et al. |
| 5,712,124 | A | 1/1998 | Walker |
| 5,824,517 | A | 10/1998 | Cleuziat et al. |
| 6,046,807 | A | 4/2000 | Chandler |
| 6,057,107 | A | 5/2000 | Fulton |
| 6,063,572 | A | 5/2000 | Ishiguro et al. |
| 6,063,603 | A | 5/2000 | Davey et al. |
| 6,117,635 | A | 9/2000 | Nazarenko |
| 6,326,145 | B1 | 12/2001 | Whitcombe et al. |
| 6,366,354 | B1 | 4/2002 | Chandler |
| 6,410,278 | B1 | 6/2002 | Notomi et al. |
| 6,420,539 | B1 | 7/2002 | Kramer et al. |
| 6,617,106 | B1 | 9/2003 | Benner |
| 6,974,670 | B2 | 12/2005 | Notomi et al. |
| 7,175,985 | B1 | 2/2007 | Kanda et al. |
| 2002/0168676 | A1 | 11/2002 | Notomi et al. |
| 2003/0073081 | A1 | 4/2003 | Mukai et al. |
| 2003/0207292 | A1 | 11/2003 | Notomi et al. |
| 2004/0038253 | A1 | 2/2004 | Nagamine |
| 2004/0132144 | A1 | 7/2004 | Notomi et al. |
| 2006/0160084 | A1 | 7/2006 | Mitani et al. |
| 2007/0190531 | A1 | 8/2007 | Mitani et al. |
| 2007/0238113 | A1 | 10/2007 | Kanda et al. |

FOREIGN PATENT DOCUMENTS

| | | | |
|---|---|---|---|
| EP | 0 519 338 | A1 | 12/1992 |
| EP | 0 648 280 | B1 | 5/1999 |
| EP | 0 971 039 | A2 | 1/2000 |
| EP | 0971039 | * | 1/2000 |
| EP | 1 020 534 | A1 | 7/2000 |
| EP | 1 041 160 | | 10/2000 |
| EP | 1 072 678 | | 1/2001 |
| EP | 1 158 047 | | 11/2001 |
| EP | 1 327 679 | | 7/2003 |
| EP | 0 754 240 | B1 | 8/2003 |
| EP | 0 971 039 | A3 | 1/2004 |
| EP | 0 576 558 | B1 | 12/2004 |
| EP | 0 726 905 | B1 | 3/2005 |
| JP | 59-93099 | | 5/1984 |
| JP | 59-148798 | | 8/1984 |
| JP | 59-204200 | | 11/1984 |
| JP | 2-5015232 | A | 5/1990 |
| JP | 4-501959 | | 4/1992 |
| JP | 5-192195 | A | 8/1993 |
| JP | 7-6986 | | 1/1995 |
| JP | 7-114718 | | 12/1995 |
| JP | 9-504699 | | 5/1997 |
| JP | 2650159 | | 5/1997 |
| JP | 2710159 | | 10/1997 |
| JP | 10-201476 | A | 8/1998 |
| JP | 10-257900 | | 9/1998 |
| JP | 11-509406 | | 8/1999 |
| JP | 2000-37194 | A | 2/2000 |
| JP | 2000-245460 | | 9/2000 |
| JP | 2000-300265 | | 10/2000 |
| JP | 2001-503973 | A | 3/2001 |
| JP | 3152927 | B2 | 4/2001 |
| JP | 2001-161486 | A | 6/2001 |
| JP | 2002-186481 | | 7/2002 |
| JP | 3313358 | B2 | 8/2002 |
| JP | 2002-345499 | A | 12/2002 |
| JP | 3313358 | B2 | 12/2002 |
| JP | 3897805 | | 1/2007 |
| WO | WO 89/01050 | A1 | 2/1989 |
| WO | WO 90/06995 | A1 | 6/1990 |
| WO | 91/13075 | | 9/1991 |
| WO | 92/15712 | | 9/1992 |
| WO | 95/12607 | | 5/1995 |
| WO | 95/12689 | | 5/1995 |
| WO | 95/21271 | | 8/1995 |
| WO | 95/25180 | | 9/1995 |
| WO | WO 96/1327 | A1 | 1/1996 |
| WO | WO9601327 | * | 1/1996 |
| WO | 97/00330 | | 1/1997 |
| WO | 97/45555 | | 12/1997 |
| WO | 98/01562 | | 1/1998 |
| WO | 98/02449 | | 1/1998 |
| WO | WO 98/14610 | A2 | 4/1998 |
| WO | 98/59066 | | 12/1998 |
| WO | 99/06591 | | 2/1999 |
| WO | 99/09211 | | 2/1999 |
| WO | 99/10369 | | 3/1999 |
| WO | 99/54455 | | 10/1999 |
| WO | 00/28082 | | 5/2000 |
| WO | 00/63691 | | 10/2000 |
| WO | 01/34838 | | 5/2001 |
| WO | 01/77317 | | 10/2001 |
| WO | 01/83817 | | 11/2001 |
| WO | 02/16639 | | 2/2002 |
| WO | 02/24902 | | 3/2002 |
| WO | WO 02/070735 | A2 | 9/2002 |
| WO | 02/077286 | | 10/2002 |

OTHER PUBLICATIONS

Pastinen et al. (Genome Research, 1997, vol. 7, p. 606-614).*

Larrick, James W., "Message Amplification Phenotyping (MAPping)—principles, practice and potential", TIBTECH May 1992, vol. 10, 146-152.

Sambrook, et al., "Conditions for Hybridization of Oligonucleotide Probes", Molecular Cloning, $2^{nd}$ edition, Cold Spring Harbor Laboratory Press, pp. 11.45-11.57, 1989.

Horlacher, et al., "Recognition by viral and cellular DNA polymerases of nucleosides bearing bases with nonstandard hydrogen bonding patterns", Proc. Natl. Acad. Sci. USA, vol. 92, pp. 6329-6333, Jul. 1995.

Sismour, et al., "First PCR amplification of DNA containing a nonstandard base pair", Biochemistry, vol. 42, No. 28, p. 8598, 2003.

Lutz, et al., "Recognition of a Non-Standard Base Pair by Thermostable DNA Polymerases", Bioorganic & Medicinal Chmistry Letters 8, pp. 1149-1152, 1998.

Gotoh, et al., "Rapid method for detection of point mutations using mismatch binding protein (MutS) and an optical biosensor", Genetic Analysis: Biomolecular Engineering, 14, pp. 47-50, 1997.

Deng, et al., Site-Directed Mutagenesis of Virtually any plasmid by Eliminating a Unique Site, Analytical Biochemistry 200, pp. 81-88, 1992.

Nakamaye, et al., "Inhibition of restriction endonuclease Nci I cleavage by phosphorothioate groups and is application to oligonucleotide-directed mutagensis", Nucleic Acids Research, vol. 14, No. 24, pp. 9679-9698, 1986.

Diaz, et al., "PCR-Mediated Chemical Mutagenesis of Cloned Duplex DNAs", BioTechniques, vol. 11, No. 2, pp. 204-211, 1991.

Radman, et al., "Mismatch Repair in *Escherichia coli*", Ann. Rev. Genet., 20, pp. 523-538, 1986.

Radman, et al., "The High Fidelity of DNA Duplication", Scientific American, pp. 24-30, Aug. 1988.

Modrich, Paul, "Methyl-directed DNA Mismatch Correction", The Journal of Biological Chemistry, vol. 264, No. 12, pp. 6597-6600, 1989.

Lahue, et al., PDNA Mismatch Correction in a Defined System, Science, vol. 245, pp. 160-164, Jul. 1989.

Jiricny, et al., "Mismatch-containing oligonucleotide duplexes bound by the *E. coli mutS*-encloded protein", Nucleic Acids Research, vol. 16, No. 16, pp. 7843-7853, 1988.

Su, et al., "Mispair Specificity of Methyl-directed DNA Mismatch Correction in Vitro", The Journal of Biological Chemistry, vol. 263, No. 14, pp. 6829-6835, May 1988.

Lahue, et al., "Methyl-directed DNA mismatch repair in *Escherichia coli*", Mutation Research, 198. pp. 37-43, 1988.

Dohet, et al., "Large non-homology in heteroduplex DNA is processed differently than single base pair mismatches", Mol Gen Gent, 206, pp. 181-184, 1987.

Jones, et al., "Repair of a Mismatch is Influenced by the Base composition of the Surrounding Nucleotide Sequence", Genetics, 115, pp. 605-610, Apr. 1987.

Lu, et al., "Repair of Single Base-Pair Transversion Mismatches of *Escherichia coli* in Vitro: Correction of Certain A/G Mismatches I s Independent of *dam* Methylation and Hose *mutHLS* Gene Functions", Genetics, 118, pp. 593-600, Apr. 1988.

Haber, et al., "Nucleotide Sequence of the *Salmonella typhimurium mutS* Gene Required for Mismatch Repair: Homology of MutS and HexA of *Streptococcus pneumoniae*", Journal of Bacteriology, vol. 170, No. 1, pp. 197-202, Jan. 1988.

Pang, et al., "Identification and Characterization of the *mutL* and *mutS* Gene Products of *Salmonella typhimurium* LT2", Journal of Bacteriology, vol. 163, No. 3, pp. 1007-1015, Sep. 1985.

Priebe, et al., "Nucleotide Sequence of the *hexA* Gene for DNA Mismatch Repair in *Streptococcus pnuemoniae* and Homology of *hexA* to *mutS* of *Escherichia coli* and *salmonella typhimurium*", Journal of Bacteriology, vol. 170, No. 1, pp. 190-196, Jan. 1988.

Smith, et al. Mutation detection with MutH, MutL, and MutS mismatch repair proteins, Proc. Natil. Acad. Sci. USA, vol. 93, pp. 4374-4379, Apr. 1996.

Au, et al., "Initiation of Methyl-directed Mismatch Repair",. The Journal of Boilogical Chemistry, vol. 267, No. 17, pp. 12142-12148, Jun. 1992.

Clark, et al., "Functional Interaction of Proliferating Cell Nuclear Antigen with HSH2-MSH6 and MSH2-MSH3 Complexes", The Journal of Biological Chemistry, vol. 275, No. 47, pp. 36498-36501, Nov. 2000.

Supplementary European Search Report issued by the European Patent Office May 15, 2008 in Application No. EP 04 80 7703.

Record of Oral Proceeding issued in the Trial Case for Invalidation of corresponding Japanese patent No. 3867926 mailed Jan. 7, 2009 with its partial English translation.

European Office Action issued in corresponding Application No. 04 807 703.6 and mailed Jun. 30, 2009—6 pages.

Notice of Trial for invalidation of JP 3-867926, dated May 20, 2008.

DNA sequence of Hepatitis B Virus of EMBL/GenBank/DDBJ database Accession No. Z72478 (Exhibit 2 of Notice of Trial dated May 20, 2008).

Nagamine, Kentaro et al. "Loop-Mediated Isothermal Amplification Reaction Using a Nondenatured Template." Clinical Chemistry 47(9), 2001, pp. 1742-1743.

Nagamine, K. et al. "Accelerateed Reaction by Loop Mediated Isothermal Amplification Using Loop Primers." Molecular and Cellular Probes, 16, 2002, pp. 223-229.

Kool, Eric T. "Synthetically modified DNAs as substrates for polymerases," Current Opinion in Chemical Biology, 4, 2000, pp. 602-608.

Notomi, Tsugubori et al. Loop-mediated isothermal amplification of DNA.: Nucleic Acids Research, 28(12), 2000, e63 (7 printed pages).

Walker, G.T. et al. "Strand Displacement Amplification—an isothermal, in vitro DNA amplification technique." Nucleic Acids Research 20(7), 1992, pp. 1691-1696.

"Third Party Observations on European Application No. 04807703.6 (EP1712618) in the name of RIKEN and Kabushiki Kaisha Dnaform" Issued by the European Patent Office Jul. 24, 2008.

Fabrice et al. "Une méthode d'amplification génique isotherme." C.R. Acad. Sci. Paris, Sciences de la vie 321, 1998, pp. 909-914.

Sambrook et al. "In Vitro Amplification of DNA by the Polymerase Chain Reaction." Molecular Cloning: A Laboratory Manual, $3^{rd}$ edition, Cold Spring Harbor Laboratory Press, 2001, pp. 8.1-8.17.

Lowe et al. "A Computer Program for Selection of oligonucleotide primers for polymerase chain reactions." Nucleic Acids Research, col. 18(7), 1990, pp. 1757-1761.

Robertson et al. "An Introduction to PCR Primer Design and Optimization of Amplification Reactions." Forensic DNA Profiling Protocols; Methods in Molecular Biology, vol. 98, 1998, pp. 121-154.

Hyndman et al. "PCR Primer Design." PCR Protocols Part III, Methods in Molecular Biology, vol. 226, 2003, pp. 81-88.

Van Pelt-Verkuil et al. Principles and Technical Aspects of PCR Amplification; Chapter 5: PCR Primers. 2008, pp. 63-90.

Puskás et al. "Reduction of mispriming in amplification reactions with restricted PCR." Genome Research, 5(3), 1995, pp. 309-311.

Haff "Improved quantitative PCR using nested primers." PCR Methods Appl., 3, 1994. pp. 332-337.

Gookin et al. Single-Tube Nested PCR for Detection of *Tritrichomonas foetus* in Feline Feces. Journal of Clinical Microbiology, vol. 40(11), 2002, pp. 4126-4130.

Chan et al. "Single-tube nested PCR in the diagnosis of tuberculosis." Journal of Clinical Pathology, vol. 49(4), 1996, 290-294.

Wolff et al. "Single-tube nested PCR with room-temperature-stable reagents." RCR Methods Appl, 4(6), 1995, pp. 376-379.

Enosawa et al. "Use of Loop-Mediated Isothermal Amplification of the IS900 Sequence for Rapid Detection of Cultured *Mycobacterium avium* subsp. *paratuberculosis*." Journal of Clinical Microbiology, 41(9), Sep. 2003, pp. 4359-4365.

"Third Party Observations on European Patent Application No. 03769966.7 in the name of RIKEN and Kabushiki Kaisha DNAform." Issued by the European Patent Office Oct. 22, 2008. (EP 03769966.7 corresponds to related application, U.S. Appl. No. 10/532,975).

Partial Oral Proceedings document for Japanese Patent No. 3867926, dispatch date Oct. 27, 2008. (JP Patent 3867926 corresponds to related application, U.S. Appl. No. 10/532,975).

Office Action issued by the Canadian Patent Office in Canadian Application No. 2,504,234 on Dec. 19, 2008. (CA 2,504,234 corresponds to related application, U.S. Appl. No. 10/532,975).

Fabrice et al, "Une méthode d'amplitication génique isotherme." C.R. Acad. Sci. Paris, Sciences de la vie 321, 1998, pp. 909-914.

Sambrook et al. "Conditions for Hybridization of Oligonucleotide Probes", Molecular Cloning: A Laboratory Manual, $2^{nd}$ edition, Cold Spring Harbor Laboratory Press, 1989, pp. 8.2-8.17.

Lowe ct al. "A Computer Program for Selection of oligonucleotide primers for polymerase chain reactions." Nucleic Acids Research, col. 18(7), 1990, pp. 1757-1761.

Robertson et al. "An Intorduction to PCR Primer Design and Optimization of Amplification Reactions." Forensic DNA Profiling Protocols; Methods in Molecular Biology, vol. 98, 1998, pp. 121-154.

Van Pelt-Verkuil et al. Principles and Technical Aspects of PCR Apmlification; Chapter 5: PCR Primers. 2008, pp. 63-90.

Puskas et al. "Reduction of mispriming in amplification reactions with restricted PCR." Genome Research, 5(3), 1995, pp. 309-311.

Haff "Improved quantitative PCR using nested primers." PCR Methods Appl., 3, 1994. pp. 332-337.

Chan et al. "Single-tube nested CPR in the diagnosis of tuberculosis." Journal of Clinical Pathology, vol. 49(4), 1996, 290-294.

Enosawa et al. "Use of Loop-Mediated Isothermal Amplifications of the IS900 Sequence for Rapid Detection of Cultured *Mycobacterium avium* subsp. *paratuberculosis*." Journal of Clinical Microbiology, 41(9), Sep. 2003, pp. 4359-4365.

DNA sequence of Hepatitis B Virus of EMBL/GenBank/DDBJ database Accession No. Z72478 (Exhibit 2 of Notiee of Trial dated May 20, 2008)

Kool, Eric T. "Synthetically modified DNAs as substrates for polymerases." Current Opinion in Chemical Biology, 4, 2000, pp. 602-608.

Walker, G.T. et al. "Strand Displacement Amplification—an isothermal; in vitro DNA amplification technique." Nucleic Acids Research 20(7), 1992, pp. 1691-1696.

Trial Decision relating to corresponding Japanese Patent No. 3867926 mailed Mar. 26, 2009 with a full English translation (123 pages).

Third Party Observations on European Application No. 04807703.6 (EP 1712618) in the name of RIKEN and Kabushiki Kaisha Dnaform dated Apr. 26, 2010—5 pages.

European Office Action issued in corresponding European Application No. 04807703.6, Mar. 10, 2010—5 pages.

Demandant's Material for Technical Illustrations Case No. 2009 (Gyo-Ke) 10107 (Suit to Cancel Trial Decision of Mukou 2008-800091 [invalidation trial case of the corresponding Japanese Patent No. 3867926]), Sep. 29, 2010, 90 pages—with an English translation.

H21 (2009) (Gyo-ke) No. 10420 Suit Against Trial Decision, Demandant's Third Brief with its English Translation—43 pages, Aug. 23, 2010.

Demandant's Material for Technical Illustrations for H21 (Gyo-Ke) 10420 (suit for cancelling trial decision of Mukou 2008-800293

[invalidation trial case of the corresponding Japanese Patent No. 3897805]), Sep. 8, 2010. 84 pages—with an English translation.
"Demandant's First Brief" for H21(2009)(Gyo-ke) No. 10420 (Suit to Cancel Trial Decision of Mukou 2008-800293 [invalidation trial case of the corresponding Japanese Patent No. 3897805]—full English translation, total 32 pages.
"Demandant's Second Brief" for H21(2009)(Gyo-ke) No. 10420 (Suit to Cancel Trial Decision of Mukou 2008-800293 [invalidation trial case of the corresponding Japanese Patent No. 3897805]—full English translation, total 24 pages.
"Description of Evidence" for H21(2009)(Gyo-ke) 10420—full English translation, total 4 pages.
"Description of Evidence (2)" for H21(2009)(Gyo-ke) 10420—full English translation, total 2 pages.
"Description of Evidence (3)" for H21 (2009)(Gyo-ke) 10420—full English translation, total 3 pages.
"Demandant's 8th Brief" for H21(2009)(Gyo-ke) No. 10107 (Suit to Cancel Trial Decision of the related Japanese Patent No. 3867926]), Dec. 22, 2010—with an English translation, total 10 pages.
"Demandant's Evidence (6)" for H21(2009)(Gyo-ke) 10107—with an English translation, total 4 pages.
"Demandant's Exibit No. 19, p. 10, II. 1-6 and FIG5" for H21(2009)(Gyo-ke) No. 10107—with a partial English translation, total 44 pages.
"Demandant's Exibit No. 20, p. 69, II. 20-23" for H21(2009)(Gyo-ke) No. 10107—with a partial English translation, total 80 pages.
"Demandant's 5th Brief" for H21(2009)(Gyo-ke) No. 10420 (Suit to Cancel Trial Decision of Mukou 2008-800293 [invalidation trial case of the corresponding Japanese Patent No. 3897805]—with an English translation, total 31 pages.
"Demandant's Description of Evidence (4)" for H21(2009)(Gyo-ke) No. 10420—with an English translation, total 4 pages.
"Demandant's 6th Brief" for H21(2009)(Gyo-ke) No. 10420 (Suit to Cancel Trial Decision of Mukou 2008-80293 [invalidation trial case of the corresponding Japanese Patent No. 3897805]—with an English translation, total 10 pages.
"Demandant's Description of Evidence (5)" for H21(2009)(Gyo-ke) No. 10420—with an English translation, total 4 pages.
Iwamoto, et al., "Loop-Mediated Isothermal Amplification for Direct Detection of Mycobacterim tuberbulosis Complex *M. avium*, and *M. intracellular* in Sputum Samples", Journal of Clinical Microbiology (2003) 41(6): 2616-2622.
Demandant's 6th Brief for H21 (Gyo-ke) 10107 (suit for canceling trial decision of Mukou 2008-800091 [invalidation trial case of JP 3867926]) Mar. 31, 2010—9 pages (see pp. 2-3 of Response filed herewith for concise explanation).
Judgment for H2I (2009) (Gyo-ke) No. 10420 Request for Cancelling Decision of Mukou 2008-800293 [invalidation trial case of the corresponding Japanese Patent No. 3897805] Oct. 11, 2011, with an English translation—46 pages.
Demandant's Exhibit No. 19—Sekiya, et al., "Recent Advances in PCR Methodology: Basic Methodology and its Application", Kyoritsu Shuppan Co., Ltd., Jun. 15, 1997, p. 437, right column, lines 5 to 9 and p. 438, right column, the last line to p. 439, left column, line 8, with an English translation.
Second Office Action in European Patent Application No. 03769966.7 corresponding to U.S. Appl. No. 10/532,975, mailed Jun. 24, 2010, 6 pages.
Demandant's 7th Brief for H21 (Gyo-Ke) 10107 (suit for cancelling trial decision of Mukou 2008-800091 [invalidation trial case of JP 3867926 corresponding to U.S. Appl. No. 10/532,975] along with a concise English explanation, 17 pages.
Second Canadian Office Action mailed Jul. 6, 2009 in Canadian Patent Application No. 2,504,234 and the response to the Office Action filed Jan. 6, 2010 (43 pages).
Third Canadian Office Action mailed Jan. 19, 2010 in Canadian Patent Application No. 2,504,234 (2 pages).
First Taiwanese Office Action mailed Nov. 11, 2009 in Taiwanese Patent Application No. 93140528 and its concise English explanation (5 pages).
Trial Decision of Makou (Invalidation) 2008-800293 (invalidation trial case of JP 3897805) and its full translation (102 pages).
Prosecution documents of Mukou (Invalidation) 2008-800293 (invalidation trial case of JP 3897805) with Demandant's Exhibit No. 14—No. 16 (247 pages).
Prosecution documents of H21 (Gyo-ke)10107 (suit for canceling trial decision of Mukou 2008-800091 [invalidation trial case of JP 3867926]) with Defendant's Exhibit No. 2-No. 7 and No. 9-No. 11 (366 pages).
Prosecution documents of H21(Gyo-Ke) 10107 (suit for canceling trial decision of Makou 2008-800091 [invalidation trial case of JP 3867926]) with Defendant's Exhibit No. 12 (44 pages).
Prosecution documents of H21 (Gyo-ke)10420 (suit for canceling trial decision of Mukou 2008-800293 [invalidation trial case of JP 3897805]) (46 pages).
Written Argument for the invalidation trial against the corresponding Japanese Patent No. 3867926 (47 pages) with its English translation (46 pages) (This document includes a Declaration of the experimental data demonstrating the effects with respect to SY160).
Demandant's 4th Brief for H21 (Gyo-Ke) 10420 (Suit to Cancel Trial Decision of Mukou 2008-800293 [invalidation trial case of the corresponding Japanese Patent No. 3897805]), Oct. 13, 2010, 16 pages—with an English translation.
Demandant's Exhibit No. 14 (Supplementary); Supplementary Fig. 2 and Fig. 3 (2 pages), 2010.
Mitani, et al., "Rapid SNP diagnostics using asymmetric isothermal amplification and a new mismatch-suppression technology", Nature Method, 2007, vol. 4, No. 3, pp. 257-262.
Parsons, et al., "Evaluation of MutS as a tool for direct measurement of point mutations in genomic DNA", Mutation Research, 1997, vol. 374, No. 2, pp. 277-285.
Notice of Trial against the corresponding Japanese patent (No. 3897805) received on Jan. 20, 2012.
Notice of Trial from corresponding Japanese patent No. 3897805 (73 pages), with its English translation—75 pages.
Reference Figures 1-4 with their English Translation.
Reference Material 1 (Written argument in JP2005-516642 dated Nov. 13, 2006)—5 pages.
Reference Material 2 (Written reply to the request for a trial for invalidation of a patent No. (invalidation) 2008-800091 dated Aug. 4, 2008)—27 pages.
Demandant's Exhibit No. 8 (Newton, et al., "Analysis of any point mutation in DNA. The amplification refractory mutation system (ARMS)", Nucleic Acids Research. vol. 17, No. 7, pp. 2503-2516, 1989).
Demandant's Exhibit No. 9 (Mukai et al. "PCR Frontier", Protein, Nucleic Acid, Enzyme, vol. 31, No. 5, pp. 425-428).
English Translation of the Notice of Trial against the corresponding Japanese patent (No. 3897805) dispatched on Jan. 19, 2012—48 pages.

* cited by examiner

FIG. 4

```
 1 aagcttttaa agcatcctca tttatgtcc aacatcagag acttaatact gaacaaatgc cacataaggg taatgactgt
                                                           ─────────────              
                                                           3' End Region of F1

81 tgaagaagat ttaacttaac atcttgcagc atcactaaga actcgcttta tactcagtgc tttggggttg ggtttg
              ─────────────                                 ─────────────
              5' End Region of R1                           3' End Region of R1
```

FIG. 8 aatact gaacaaatgc cacatanaga taatgactgt tgangangat ttanctianc atcttgcagc atcactaaga actgactta tactcagttg tttgcctta ag↑

↓
g
Mutated Portion

3' End Region of F1
5' End Region of R1 or R1G
3' End Region of R1 or R1G

FIG. 10

```
1  aagcttttaa agcatcctca ttttatgtcc aacatcagag acttaatact gaacaaatgc cacataaagg taatgactgt
                                                                  ───────────────────────→
                                                                  3' End Region of F1              3R 81 tgaagaagat ttaacttaac atcttgcagc atcactaaga actcgcttta tactcagtgc ttttggttg ggtttg
                        ─────────────────────────────                ────────────────
                        5' End Region of R1                          3' End Region of R1
                                              3F
```

A

Without MutS

B

With MutS

METHOD OF AMPLIFYING NUCLEIC ACID AND METHOD OF DETECTING MUTATED NUCLEIC ACID USING THE SAME

CROSS REFERENCE TO RELATED APPLICATIONS

This patent application claims priority based on Japanese Patent Application Nos. JP2003-431003 (filed on Dec. 25, 2003) and JP2004-313910 (filed on Oct. 28, 2004) that are patent applications filed previously in Japan. These previous patent applications are incorporated herein by reference in their entireties.

BACKGROUND OF THE INVENTION

1. Technical Field

The present invention relates to a method of amplifying a nucleic acid sequence that is useful in the field of genetic engineering. More particularly, the present invention relates to a method of amplifying a nucleic acid sequence that utilizes a strand displacement reaction, and a mutation detection method using the same.

2. Background Art

In the field of genetic engineering, an assay based on the complementation of nucleic acid sequences is known as a method that allows genetic features to be analyzed directly. In such an assay, when a target (aimed) gene is present only in a small amount in a sample, the detection thereof generally is not easy. It therefore is necessary to amplify the target gene itself beforehand.

The amplification of the target gene (nucleic acid amplification) mainly is carried out by an enzymatic method with the use of DNA polymerase. Major examples of such an enzymatic method include the polymerase chain reaction method (PCR method; U.S. Pat. Nos. 4,683,195, 4,683,202, and 4,800,159) and the reverse transcription PCR method (RT-PCR method; Trends in Biotechnology 10, pp 146-152, 1992) that is a combination of the PCR method and a reverse transcriptase reaction. These methods allow a target gene derived from DNA or RNA to be amplified by repeating a reaction that consists of three steps. The three steps include: the dissociation (denaturation) of a double-stranded nucleic acid into a single-stranded nucleic acid to serve as a template; the annealing of a primer to the single-stranded nucleic acid; and the synthesis (extension) of a complementary strand from the primer. These methods require the repetition of three steps in total in which the reaction solution is adjusted to a temperature suitable for each reaction in the three steps described above.

Furthermore, EP 0320308 A discloses the ligase chain reaction method (LCR method). In this method, a known gene sequence is amplified by conducting a two-step temperature cycling reaction (a heating-cooling repeated reaction) using a thermostable DNA ligase.

However, the methods described above require the use of an expensive thermal cycler that can control temperature strictly over time in a wide range of temperatures. Since the above-mentioned reactions are conducted under two to three temperature conditions, time is required to make an adjustment to each reaction temperature. Hence, the time required for the adjustment increases as the number of cycles increases.

In order to solve the above-mentioned problems, nucleic acid amplification methods have been developed that can be carried out isothermally. Examples of such methods include: the strand displacement amplification (SDA) method described in JP7(1995)-114718B; the self-sustained sequence replication (3SR) method; the nucleic acid sequence based amplification (NASBA) method described in Japanese Patent No. 2650159; the transcription-mediated amplification (TMA) method; the Q-beta replicase method described in Japanese Patent No. 2710159; various improved SDA methods described in U.S. Pat. No. 5,824,517, WO99/09211, and WO 95/25180; the loop-mediated isothermal amplification (LAMP) method described in WO00/28082; and the isothermal and chimeric primer initiated amplification of nucleic acids (ICAN method) described in WO02/16639. The reactions in all the steps involved in the isothermal nucleic acid amplification methods described above proceed simultaneously in a reaction mixture maintained at a constant temperature.

In the SDA method, a target nucleic acid (and a complementary strand thereto) in a sample can be amplified through the displacement of a double strand mediated by a DNA polymerase and a restriction endonuclease in a system where DNA is amplified finally. This method requires four primers, two of which need to be designed so as to contain a recognition site for the restriction endonuclease. Furthermore, this method requires a modified deoxynucleotide triphosphate as a substrate for nucleic acid synthesis. The modified deoxynucleotide triphosphate is, for instance, a deoxynucleotide triphosphate in which the oxygen atom of the phosphate group located at the alpha position of the triphosphate moiety has been substituted by a sulfur atom (S). Accordingly, this method requires high running cost. Moreover, in this method, the amplified nucleic acid fragment contains a modified nucleotide such as an alpha-S-displaced deoxynucleotide. Hence, for example, when the amplified fragment is subjected to a restriction enzyme fragment length polymorphism (RFLP) assay, the amplified fragment cannot be cleaved by a restriction enzyme and thus such an assay cannot be conducted in some cases.

The improved SDA method described in U.S. Pat. No. 5,824,517 requires a chimeric primer that is composed of RNA and DNA, with the DNA being located on the 3' end side. Such a chimeric primer that is composed of RNA and DNA is difficult to synthesize. Furthermore, in order to handle a primer containing RNA, professional skills are required. Furthermore, the improved SDA method described in WO99/09211 requires a restriction enzyme that produces a 5' protruding end. Moreover, the improved SDA method described in WO95/25180 requires at least two pairs of primers. Hence, these methods require high running cost.

In the ICAN method, it is necessary to use a chimeric primer as well as an RNaseH. The chimeric primer is composed of RNA and DNA, with the RNA being located on the 3' end side. The RNaseH cleaves the RNA moiety located at the 3' end of the primer. Accordingly, an increased number of reagents are used and longer processing time also is necessary. Thus the ICAN method is not suitable for processing a large amount of samples.

In the LAMP method, four primers are necessary. They recognize six regions, so that a target gene can be amplified. That is, in this method, a first primer anneals to a template strand to cause extension, and then the extended strand produced by the first primer separates from the template strand due to the strand displacement reaction caused by a second primer designed upstream from the first primer. At this time, a stem-loop structure is formed in the 5' end portion of the extended strand due to the structure of the first-primer extension product that has been removed. Similar reactions occur in the other strand of the double-stranded nucleic acid or on the 3' end side of the first-primer extension product that has been removed. These reactions are repeated and thereby the target nucleic acid is amplified. Hence, in the LAMP method, the action mechanism of the amplification reaction is complicated and furthermore, six regions must be selected. This makes it difficult to design the primers. Moreover, two of the four primers are required to be relatively long chain primers. Accordingly, the synthesis and purification of the primers are complicated and reagents are difficult to prepare.

There is a need for a nucleic acid amplification method that can be carried out at lower running cost and that allows a nucleic acid fragment obtained thereby further to be used for genetic engineering treatments. Particularly, an isothermal nucleic acid amplification method is desired that allows amplification to be conducted quickly with a pair of primers.

When a single nucleotide mutation that is present in a target nucleic acid is to be detected using such an amplification method as described above, various problems have arisen. For instance, in the mutation detection by the PCR-SSP method based on the PCR method, a primer is used that has a nucleotide associated with a mutation at the 3' end, and the mutation is detected depending on the presence or absence of an amplification product. In an amplification reaction caused by such a primer, however, even when the nucleotide associated with a mutation and the nucleotide located at the 3' end of the primer are not complementary to each other, an extension reaction may occur erroneously. In the PCR method, a double-stranded nucleic acid synthesized through the extension reaction of a primer is used as a new template. In this case, the sequence to which the next new primer anneals is not the nucleotide sequence that has been contained originally in the sample but a copy of the primer sequence. Accordingly, even if the complementary strand synthesis of a wrong region occurs only once, the wrong region is amplified one after another. Hence, amplification products other than those intended to be obtained are produced readily. Thus, it is difficult to detect a single nucleotide mutation correctly.

Furthermore, in the PCR-SSO method, a probe DNA that can hybridize to a region containing a mutated site is brought into contact with a target amplification product obtained through amplification performed by the PCR method. Then it is observed whether hybridization occurs or not and thereby the presence or absence of a mutation in the target amplification product is determined. In this method, however, beside the longer hybridization reaction time, problem is a specificity. For example, nonspecific hybridization may take place depending on the stringency of the reaction solution. Thus it is not easy to check the mutation of a single base accurately.

Another mutation detection UCAN method is based on ICAN method where a DNA-RNA-DNA chimeric primer is used that contains a nucleotide associated with a mutation in a RNA portion. The DNA located at the 3' end of this chimeric primer has been modified chemically so that no extension reaction occurs therefrom. In the case where an amplification reaction is conducted in a reaction solution containing such a chimeric primer and RNaseH, the RNaseH cleaves the RNA portion only when the sequence of the chimeric primer and that of the template match completely with each other. In that case, an extension reaction starts from the 3' end of a newly produced primer and thereby the template DNA is amplified. On the other hand, when the sequence of the chimeric primer and that of the template DNA do not match with each other, i.e. when a mutation exists, the RNA portion is not cleaved by RNaseH. In this case, the 3' end of the chimeric primer remains chemically modified. Thus DNA amplification does not occur. However, in both the ICAN and UCAN methods, the amplification is performed through specific hybridization to two regions of a template as in the conventional PCR method. Hence, there is a problem in the specificity. Accordingly, after the amplification, it is necessary further to check whether the amplification product obtained is a target one. Thus it takes a long time until the examination results are obtained. In addition, the syntheses of the modified primer, the chimeric primer, etc. are complicated.

In the LAMP method, at least four primers are necessary. Accordingly, for example, a primer dimer tends to be produced. Furthermore, since six specific regions are necessary, the primers are very difficult to design. Hence, it takes a long time to study the conditions that improve the specificity of nucleic acid amplification, for example. Moreover, in the mutation detection that is performed by the LAMP method described in WO01/034838, a mutation is recognized at the 3' end of a dumbbell structure that is an amplification product produced during the amplification. In this method, it is considered that when a mutation exists at the 3' end of the dumbbell structure, the extension reaction stops occurring therefrom, which inhibits the target region from being amplified. However, like the case of the PCR-SSP method, a mismatch of one base located at the 3' end does not always stop the extension reaction. Even when no amplification occurs from the 3' end of the dumbbell structure, the amplification product itself already has formed a dumbbell structure. Accordingly, a stem-loop structure of itself has been formed, and therefore the primer anneals to the loop structure portion. Thus the extension reaction that occurs from the 3' end of the primer always is conducted. It therefore is very difficult to identify the single nucleotide mutation based on whether or not the amplification has occurred.

Recently, great importance has been attached to diagnostic techniques for quickly detecting gene information such as gene insertion, gene deletion, etc. Particularly, importance is attached to a technique for analyzing a target gene easily, quickly, and accurately, for instance, a technique for specifically detecting a gene marker or mRNA that is expressed specifically to cancer cells, etc.

When mRNA is to be detected that has been expressed specifically to only a specific cell type, such as a cancer cell, a nucleic acid sample that commonly is used includes not only target mRNA but also genomic DNA intermingled therein. The nucleotide sequence of mRNA is one obtained by removing sequences of some intron portions from the nucleotide sequence of genomic DNA. One intron generally has a strand length of several bases to several hundreds of bases. When using such a nucleic acid sample as a template and a primer like the one that is used in the PCR method, both mRNA and genomic DNA can serve as templates. Hence, amplification occurs from both templates. Even when the primer is designed so as to allow mRNA to be amplified specifically, amplification generally occurs not only from mRNA but also from genomic DNA in a nucleic acid sample containing genomic DNA intermingled therein, since the sequence of mRNA is a part of the sequence of genomic DNA. Accordingly, mRNA cannot be amplified specifically. Furthermore, it is considered to be very difficult to amplify such mRNA accurately and quantitate mRNA present in the sample. Moreover, in the case of amplifying a target nucleic acid in which an insertion or deletion of several bases to several hundreds of bases exists and then determining the presence or absence of the amplification product thereof, it is very difficult to recognize a small difference in size when the band of a target amplification product is checked by the electrophoresis method that has been employed conventionally. When gene diagnosis is performed at a clinical site, it is necessary to process many samples simply and efficiently in a short time. Hence, the conventional methods cannot deal with this sufficiently.

DISCLOSURE OF INVENTION

The present inventors have found out the following. That is, in a method of amplifying a nucleic acid utilizing a strand displacement reaction, when a primer that allows a stem-loop to be formed only when the target nucleic acid is amplified is designed to satisfy particular conditions and then this primer and a primer having a folded sequence in its 5' end portion are used in combination, the target nucleic acid can be amplified specifically and efficiently.

The present invention therefore is intended to provide a primer set that allows a target nucleic acid to be amplified specifically and efficiently, and a method of amplifying a nucleic acid using the same.

A primer set according to the present invention includes at least two primers that allow a target nucleic acid sequence to be amplified. A first primer included in the primer set contains, in its 3' end portion, a sequence (Ac') that hybridizes to a sequence (A) located in the 3' end portion of the target nucleic acid sequence, and also contains, on the 5' side of the sequence (Ac'), a sequence (B') that hybridizes to a complementary sequence (Bc) to a sequence (B) that is present on the 5' side with respect to the sequence (A) in the target nucleic acid sequence. A second primer included in the primer set contains, in its 3' end portion, a sequence (Cc') that hybridizes to a sequence (C) located in the 3' end portion of a complementary sequence to the target nucleic acid sequence, and also contains, on the 5' side of the sequence (Cc'), a folded sequence (D-Dc') that contains, on the same strand, two nucleic acid sequences that hybridize to each other.

Furthermore, a nucleic acid amplification method of the present invention is a method of amplifying a target nucleic acid sequence contained in a template nucleic acid. The method includes: (a) preparing a template nucleic acid containing a target nucleic acid sequence; (b) preparing a primer set according to the present invention; and (c) performing a nucleic acid amplification reaction in the presence of the template nucleic acid using the primer set.

According to the present invention, a target nucleic acid can be synthesized continuously under an isothermal condition, with DNA or RNA being used as a template. Hence, the primer set and the nucleic acid amplification method using the same according to the present invention require neither special apparatuses such as a thermal cycler nor the time for temperature adjustment. This allows an amplification product to be obtained in a shorter time. Furthermore, the primer set of the present invention allows a nucleic acid to be amplified highly specifically. Accordingly, the use of this makes it possible to determine, by detecting amplification products, the presence or absence of a mutation in a gene, particularly, a single nucleotide mutation, the presence or absence of a deletion or insertion of a sequence in a particular nucleic acid sequence, etc.

Furthermore, the present inventors have found out the following. That is, in a mutation detection method that utilizes a nucleic acid amplification reaction to be performed isothermally using a nucleic acid reagent that causes a mismatch with a template depending on either the presence or absence of a mutation in the template, a mutation can be detected more accurately by performing the nucleic acid amplification reaction in the presence of a substance having mismatch recognition ability.

Thus a second aspect of the current invention provides a method of determining the presence or absence of a mutation in a nucleic acid sequence contained in a nucleic acid sample by isothermally performing a nucleic acid amplification reaction using a nucleic acid reagent that causes a mismatch with a template depending on either the presence or absence of a mutation in the template, in the presence of a substance having mismatch recognition ability such as a mismatch binding protein.

BRIEF DESCRIPTION OF DRAWINGS

FIG. 4 shows the locations, on a human STS DYS237 gene, of first and second primers used for amplifying the gene.

FIG. 8 shows a sequence containing a single nucleotide mutation and sequences that are free from it, which were produced with respect to a specific region of the human STS DYS237 gene.

FIG. 10 shows the locations, on the human STS DYS237 gene, of the first primer, the second primer, and third primers used for amplifying the gene.

DESCRIPTION OF THE INVENTION

The primer set of the present invention includes at least two primers that allow a target nucleic acid sequence to be amplified. A first primer included in the primer set contains, in its 3' end portion, a sequence (Ac') that hybridizes to a sequence (A) located in the 3' end portion of the target nucleic acid sequence, and also contains, on the 5' side of the sequence (Ac'), a sequence (B') that hybridizes to a complementary sequence (Bc) to a sequence (B) that is present on the 5' side with respect to the sequence (A) in the target nucleic acid sequence. Furthermore, a second primer included in the primer set contains, in its 3' end portion, a sequence (Cc') that hybridizes to a sequence (C) located in the 3' end portion of a complementary sequence to the target nucleic acid sequence, and also contains, on the 5' side of the sequence (Cc'), a folded sequence (D-Dc') that contains, on the same strand, two nucleic acid sequences that hybridize to each other.

In the present invention, the term "target nucleic acid" or "target nucleic acid sequence" denotes not only the nucleic acid or sequence thereof itself that is intended to be amplified but also a sequence complementary thereto or a nucleic acid having that sequence.

In the present invention, the term "hybridize" denotes that a part of a primer according to the present invention hybridizes to a target nucleic acid under a stringent condition but does not hybridize to nucleic acid molecules other than the target nucleic acid. The stringent condition can be determined depending on the melting temperature Tm (° C.) of a double strand formed of a primer according to the present invention and a complementary strand thereto, the salt concentration of a hybridization solution, etc. For example, reference can be made to J. Sambrook, E. F. Frisch, T. Maniatis; Molecular Cloning 2nd edition, Cold Spring Harbor Laboratory (1989), etc. For instance, when hybridization is carried out at a slightly lower temperature than the melting temperature of a primer to be used, the primer is allowed to hybridize to a target nucleic acid specifically. Such a primer can be designed using commercially available primer construction software, for example, Primer3 (manufactured by Whitehead Institute for Biomedical Research). According to a preferred embodiment of the present invention, a primer that hybridizes to a certain target nucleic acid contains the sequence of all or a part of the nucleic acid molecules complementary to the target nucleic acid.

Figure 1:
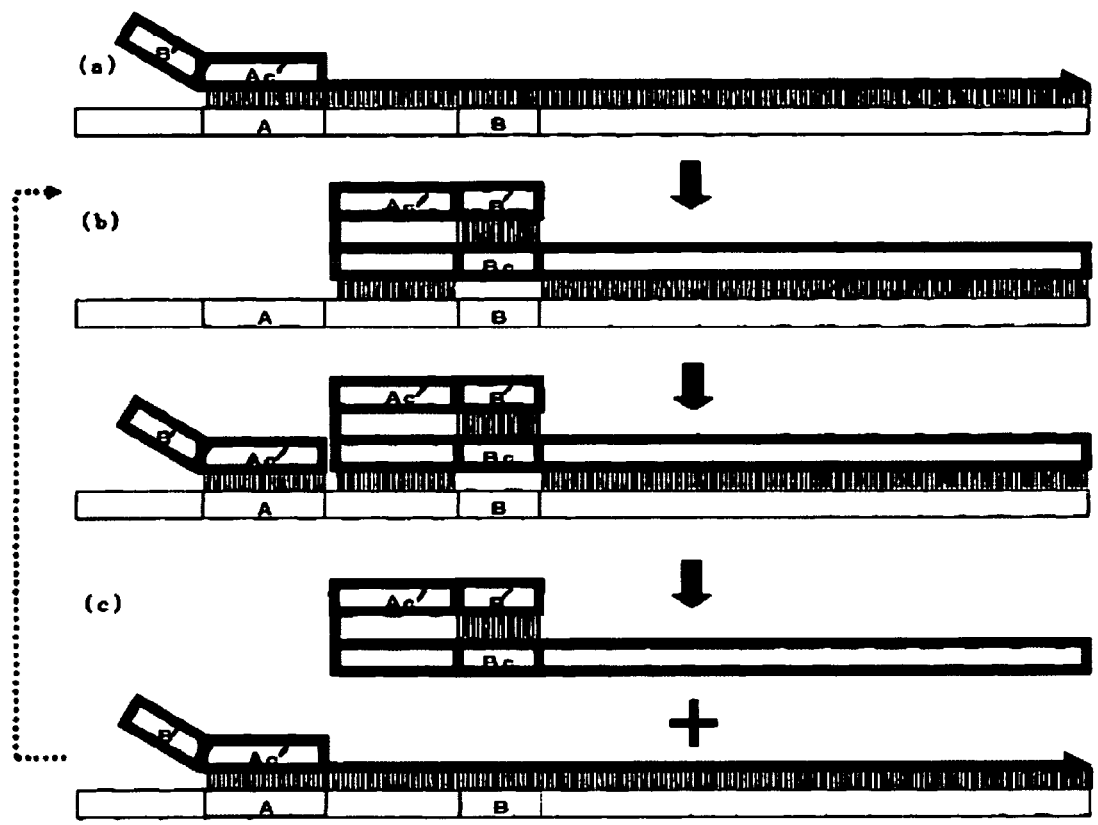
FIG. 1 is a diagram that schematically shows the action mechanism of a nucleic acid amplification reaction to be conducted using a first primer according to the present invention.

FIG. 1 schematically shows the action mechanism of nucleic acid synthesis to be conducted using the first primer. First, a target nucleic acid sequence contained in a nucleic acid to serve as a template is determined. Then the sequence (A) that is located in the 3' end portion of the target nucleic acid sequence as well as the sequence (B) that is present on the 5' side with respect to the sequence (A) are determined. The first primer contains the sequence (Ac') and further contains the sequence (B') on the 5' side thereof. The sequence (Ac') hybridizes to the sequence (A) while the sequence (B') hybridizes to the complementary sequence (Bc) to the sequence (B). In this case, the first primer may contain an intervening sequence that does not affect the reaction, between the sequence (Ac') and the sequence (B'). Annealing of such a primer to the template nucleic acid results in a state where the sequence (Ac') of the primer has hybridized to the sequence (A) of the target nucleic acid sequence (FIG. 1(a)). When a primer extension reaction occurs in this state, a nucleic acid containing the complementary sequence to the target nucleic acid sequence is synthesized. Then the sequence (B') that is present on the 5' end side of the nucleic acid thus synthesized hybridizes to the sequence (Bc) that is present in the nucleic acid. This allows a stem-loop structure to be formed in the 5' end portion of the nucleic acid synthesized as described above. As a result, the sequence (A) located on the template nucleic acid becomes a single strand and then another primer having the same sequence as that of the preceding first primer hybridizes thereto (FIG. 1(b)). Thereafter, an extension reaction occurs from the newly hybridized first primer due to the strand displacement reaction. At the same time, the nucleic acid synthesized previously is dissociated from the template nucleic acid (FIG. 1(c)).

In the action mechanism described above, the phenomenon that the sequence (B') hybridizes to the sequence (Bc) typically occurs due to the presence of the complementary regions on the same strand. Generally, when a double-stranded nucleic acid is dissociated into a single strand, partial dissociation starts from the ends thereof or from the relatively unstable portions other than the ends. In the double-stranded nucleic acid produced through the extension reaction caused by the above-mentioned first primer, base pairs located in the end portion are in a state of equilibrium between dissociation and binding at relatively high temperatures and thereby a double strand is retained as a whole. In such a state, when a sequence complementary to the dissociated portion located at the end is present on the same strand, a stem-loop structure can be formed in a metastable state. This stem-loop structure does not exist stably. However, another identical primer binds to the complementary strand portion (the sequence (A) on the template nucleic acid) exposed due to the formation of the stem-loop structure, and thereby a polymerase causes the extension reaction immediately. Accordingly, while the strand synthesized previously is displaced and thereby is released, a new double-stranded nucleic acid can be produced at the same time.

The design criteria for the first primer according to a preferred aspect of the present invention are as follows. First, in order for a new primer to anneal to the template nucleic acid efficiently after a complementary strand to the template nucleic acid is synthesized through the extension of the primer, it is necessary to allow the sequence (A) portion located on the template nucleic acid to be a single strand through the formation of the stem-loop structure at the 5' end of the complementary strand synthesized as described above. For that purpose, a ratio of (X−Y)/X is important. That is a ratio of the difference (X−Y) to the number X, wherein X denotes the number of bases contained in the sequence (Ac') while Y indicates the number of bases contained in the region flanked by the sequence (A) and the sequence (B) in the target nucleic acid sequence. However, the portion that is present on the 5' side with respect to the sequence (A) on the template nucleic acid and that is unrelated to the hybridization of the primer is not required to be a single strand. Furthermore, in order for a new primer to anneal to the template nucleic acid efficiently, it also is necessary that the above-mentioned stem-loop structure be formed efficiently. For the efficient formation of the stem-loop structure, i.e. for efficient hybridization between the sequence (B') and the sequence (Bc), the distance (X+Y) between the sequence (B') and the sequence (Bc) is important. Generally, the optimal temperature for the primer extension reaction is a maximum of around 72° C. It is difficult to dissociate the extended strand over a long region at such low temperatures. Hence, conceivably, in order for the sequence (B') to hybridize to the sequence (Bc) efficiently, it is preferable that a smaller number of bases exist between both the sequences. On the other hand, conceivably, in order for the sequence (B') to hybridize to the sequence (Bc) to allow the sequence (A) portion located on the template nucleic acid to be a single strand, it is preferable that a larger number of bases exist between the sequence (B') and the sequence (Bc).

From such viewpoints as described above, the aforementioned first primer according to the preferred embodiment of the present invention is designed so that the ratio (X−Y)/X is at least −1.00, preferably at least 0.00, more preferably at least 0.05, and further preferably at least 0.10 but is 1.00 or lower, preferably 0.75 or lower, more preferably 0.50 or lower, and further preferably 0.25 or lower, in the case where no intervening sequence is present between the sequence (Ac') and the sequence (B') that compose the primer. Moreover, the distance (X+Y) is preferably at least 15, more preferably at least 20, and further preferably at least 30 but is preferably 50 or less, more preferably 48 or less, and further preferably 42 or less.

When an intervening sequence (the number of bases contained therein is Y') is present between the sequence (Ac') and the sequence (B') that compose the primer, the first primer according to the preferred embodiment of the present invention is designed so that the ratio {X−(Y−Y')}/X is at least −1.00, preferably at least 0.00, more preferably at least 0.05, and further preferably at least 0.10 but is 1.00 or lower, preferably 0.75 or lower, more preferably 0.50 or lower, and further preferably 0.25 or lower. Moreover, the distance (X+Y+Y') is preferably at least 15, more preferably at least 20, and further preferably at least 30 but is preferably 100 or less, more preferably 75 or less, and further preferably 50 or less.

The aforementioned first primer has a strand length that enables base pairing with the target nucleic acid while allowing the necessary specificity to be maintained under given conditions. The strand length of this primer is preferably 15 to 100 nucleotides and more preferably 20 to 60 nucleotides. The lengths of the sequence (Ac') and the sequence (B') that compose the first primer each are preferably 5 to 50 nucleotides and more preferably 7 to 30 nucleotides. Furthermore, an intervening sequence that does not affect the reaction may be inserted between the sequence (Ac') and the sequence (B') if necessary.

Figure 2:
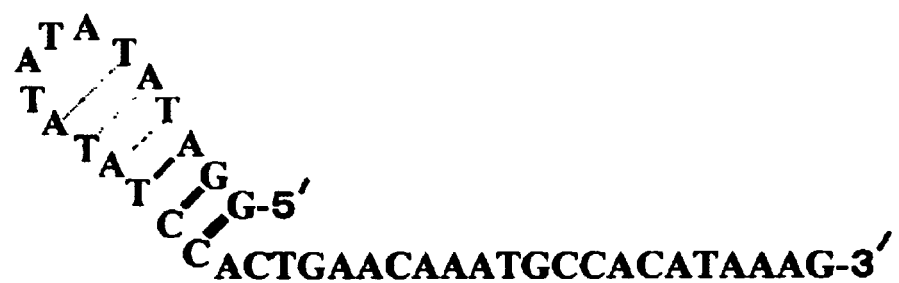
FIG. 2 shows an example of the structure of a second primer according to the present invention.

As described above, the second primer included in the primer set according to the present invention contains, in its 3' end portion, a sequence (Cc') that hybridizes to a sequence (C) located in the 3' end portion of a complementary sequence (the strand located on the opposite side to the strand to which the first primer hybridizes) to the target nucleic acid sequence. The second primer also contains, on the 5' side of the sequence (Cc'), a folded sequence (D-Dc') that contains, on the same strand, two nucleic acid sequences that hybridize to each other. Such a second primer has a structure like the one shown in FIG. 2, for example. However, the sequence and the number of nucleotides of the second primer are not limited to those shown in FIG. 2. The length of the sequence (Cc') of the second primer is preferably 5 to 50 nucleotides and more preferably 10 to 30 nucleotides. On the other hand, the length of the folded sequence (D-Dc') is preferably 2 to 1000 nucleotides, more preferably 2 to 100 nucleotides, further preferably 4 to 60 nucleotides, and still further preferably 6 to 40 nucleotides. The number of nucleotides of the base pairs that are formed through hybridization that occurs in the folded sequence is preferably 2 to 500 bp, more preferably 2 to 50 bp, further preferably 2 to 30 bp, and still further preferably 3 to 20 bp. The nucleotide sequence of the folded sequence (D-Dc') may be any sequence and is not particularly limited. However, it is preferable that the nucleotide sequence be one that does not hybridize to the target nucleic acid sequence. In addition, an intervening sequence that does not affect the reaction may be inserted between the sequence (Cc') and the folded sequence (D-Dc') if necessary.

Figure 3A:
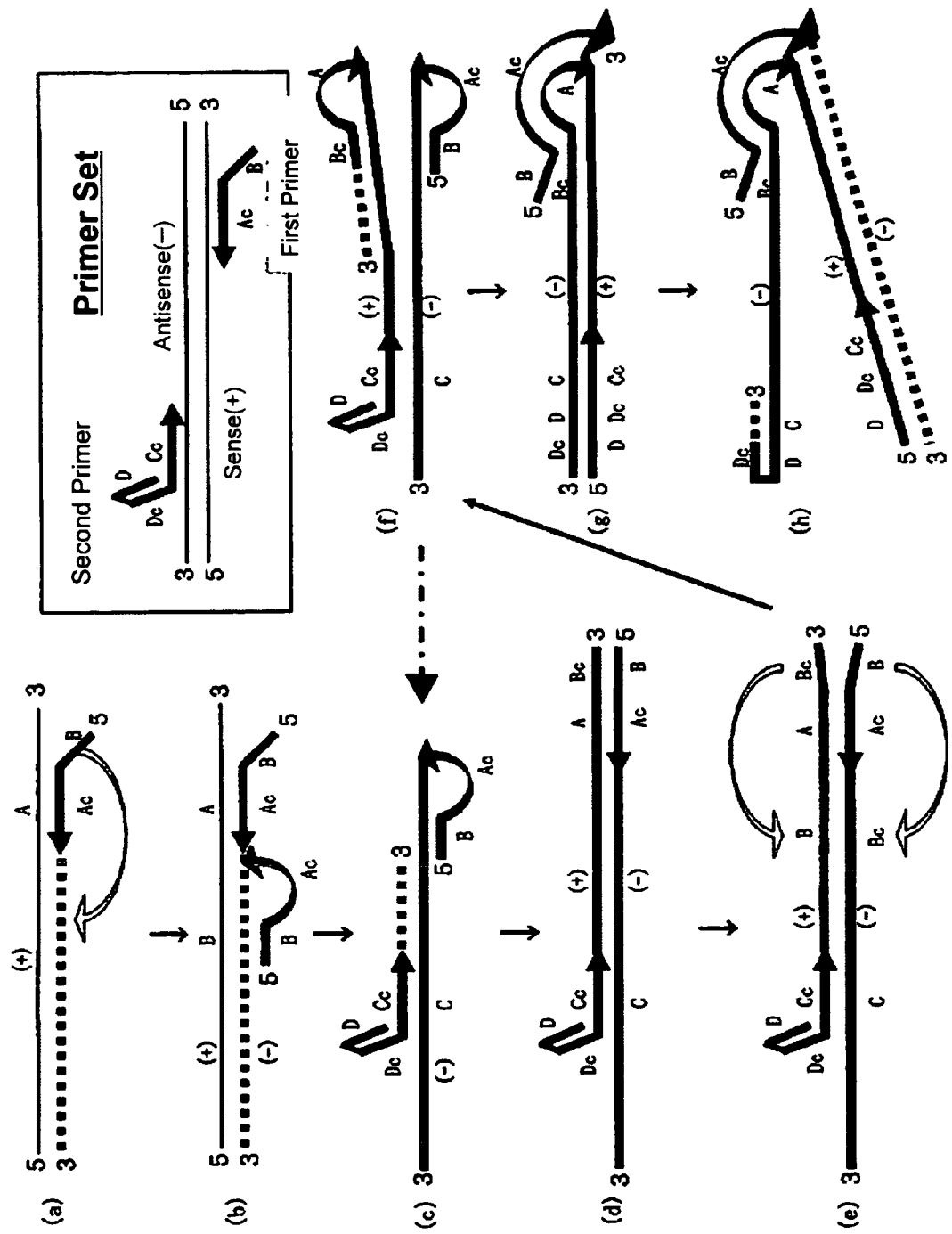
FIG. 3a schematically shows the action mechanism of a nucleic acid amplification reaction to be conducted using the first primer and the second primer according to the present invention.
Figure 3B:
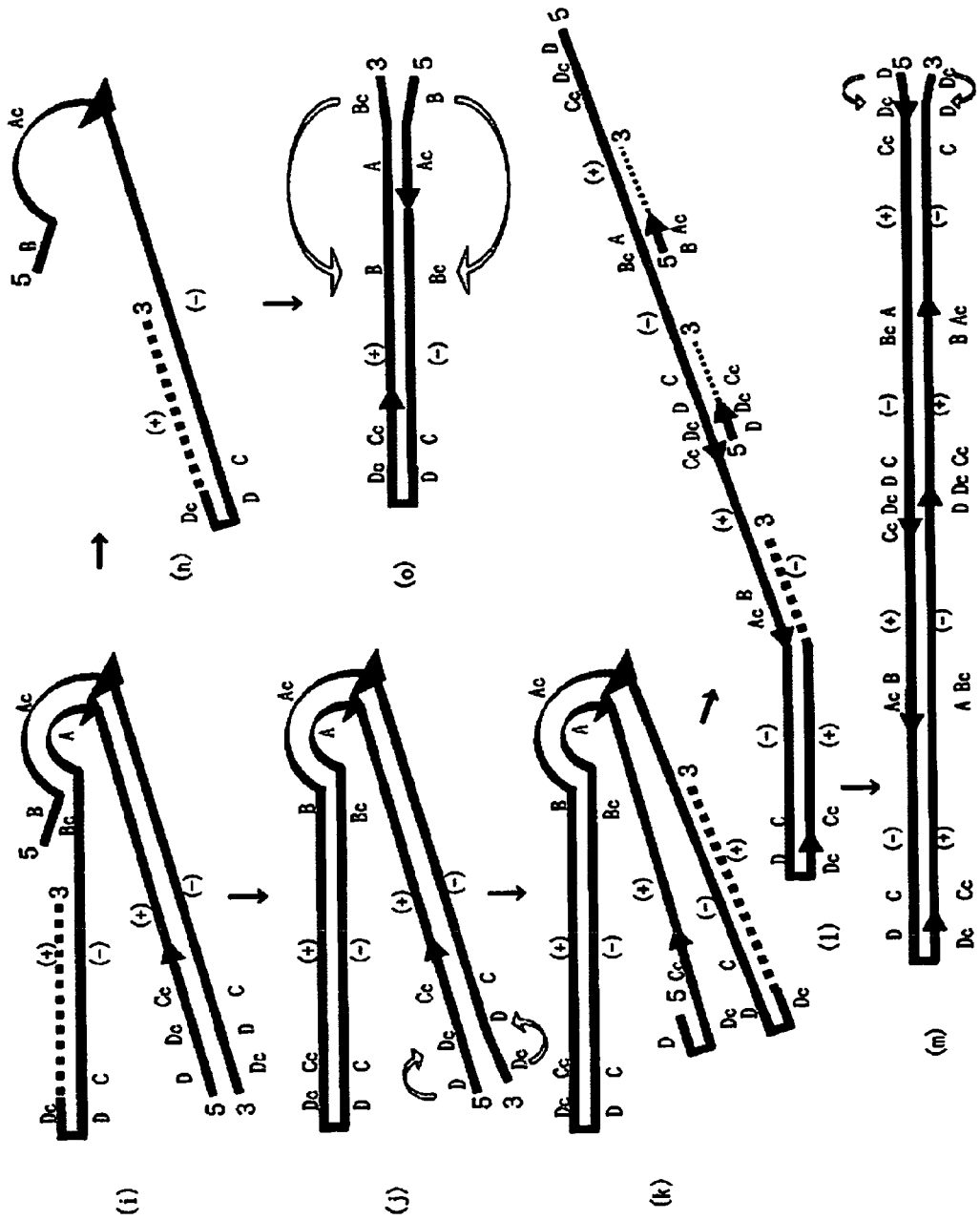
FIG. 3b schematically shows the action mechanism of the nucleic acid amplification reaction to be conducted using the first primer and the second primer according to the present invention.

A conceivable action mechanism of the nucleic acid amplification reaction that is caused by the above-mentioned first primer and second primer is described with reference to FIG. 3 (FIGS. 3a and 3b). In FIG. 3, in order to simplify the description, two sequences that hybridize to each other are described as sequences that are complementary to each other. However, the present invention is not limited thereto. First, the first primer hybridizes to a sense strand of a target nucleic acid and thereby the extension reaction of that primer occurs (FIG. 3(a)). Subsequently, a stem-loop structure is formed on the extended strand (−) and thereby the sequence (A) on the target nucleic acid sense strand is allowed to be a single strand. Then a new first primer hybridizes to the sequence (A) (FIG. 3(b)). This causes the extension reaction of the primer and then the extended strand (−) synthesized previously is dissociated. Next, the second primer hybridizes to the sequence (C) located on the dissociated extended strand (−) (FIG. 3(c)). This causes the extension reaction of the primer and thereby an extended strand (+) is synthesized (FIG. 3(d)). Stem-loop structures are formed at the 3' end of the extended strand (+) thus synthesized and at the 5' end of the extended strand (−) (FIG. 3(e)). Then the extension reaction occurs from the loop end of the extended strand (+) that is the 3' end of the free form and at the same time, the extended strand (−) is dissociated (FIG. 3(f)). The extension reaction that has occurred from the loop end results in production of a hairpin-type double-stranded nucleic acid to which the extended strand (−) has bound on the 3' side of the extended strand (+) through the sequence (A) and the sequence (Bc). Then the first primer hybridizes to the sequence (A) and the sequence (Bc) (FIG. 3(g)) and the extension reaction caused thereby allows the extended strand (−) to be produced (FIGS. 3(h) and 3(i)). Furthermore, the folded sequence that is present at the 3' end of the hairpin-type double-stranded nucleic acid provides the 3' end of the free form (FIG. 3(h)). Then the extension reaction caused therefrom (FIG. 3(i)) allows a single-stranded nucleic acid to be produced (FIG. 3(j)). The single-stranded nucleic acid has the folded sequence at each end thereof and contains the extended strand (+) and the extended strand (−) alternately via the sequences derived from the first and second primers. In this single-stranded nucleic acid, the folded sequence that is present at the 3' end thereof provides the 3' end (the starting point for complementary strand synthesis) of the free form (FIG. 3(k)). Accordingly, the similar extension reaction is repeated and the strand length is doubled per extension reaction (FIG. 3(l) and 3(m)). In the extended strand (−) synthesized from the first primer that has been dissociated in FIG. 3(i), the folded sequence that is present at the 3' end thereof provides the 3' end (the starting point for complementary strand synthesis) of the free form (FIG. 3(n)). Accordingly, the extension reaction caused therefrom allows stem-loop structures to be formed at both ends and thereby a single-stranded nucleic acid is produced (FIG. 3(o)). The single-stranded nucleic acid contains the extended strand (+) and the extended strand (−) alternately via the sequences derived from the primers. Similarly in this single-stranded nucleic acid, the formation of a loop at the 3' end provides the starting point for complementary strand synthesis successively. Hence, the extension reaction therefrom occurs in succession. Thus in the single-stranded nucleic acid that is extended automatically in such a manner, the sequences derived from the first primer and the second primer are contained between the extended strand (+) and the extended strand (−). Accordingly, each primer can hybridize to cause the extension reaction. This allows the sense strand and the antisense strand of the target nucleic acid to be amplified considerably.

The primer set according to the present invention may include a third primer in addition to the first primer and the second primer. The third primer hybridizes to the target nucleic acid sequence or the complementary sequence thereto. However, the third primer does not compete with other primers for hybridization to the target nucleic acid sequence or the complementary sequence thereto.

In the present invention, the expression "does not compete" denotes that even when the primer hybridizes to a target nucleic acid, other primers are not hindered from providing starting points for complementary strand synthesis.

When the target nucleic acid has been amplified with the first primer and the second primer, the amplification product contains the target nucleic acid sequence and the complementary sequence thereto alternately as described above. The amplification product has a folded sequence or a loop structure that is present at its 3' end. It provides the starting point for complementary strand synthesis and thereby extension reactions occur successively therefrom. When such an amplification product becomes a single strand partially, the third primer can anneal to the target sequence that is present in the single strand portion. This allows the target nucleic acid sequence contained in the amplification product to be provided with a new starting point for complementary strand synthesis. Then an extension reaction occurs therefrom. Thus the nucleic acid amplification reaction is performed much quicker.

The third primer is not always limited to one type. In order to improve the speed and specificity of the nucleic acid amplification reaction, two or more of third primers may be used simultaneously. Typically, such third primers have different sequences from those of the first primer and the second primer. However, each of the third primers may hybridize to a region, a part of which is hybridized by the first or second primer, as long as they do not compete with the first or second primer. The strand length of the third primer is preferably 2 to 100 nucleotides, more preferably 5 to 50 nucleotides, and further preferably 7 to 30 nucleotides.

The third primer is intended mainly to provide an auxiliary function to advance the nucleic acid amplification reaction much quicker that is caused by the first primer and the second primer. Hence, it is preferable that the third primer have a lower Tm than that of each 3' end of the first primer and the second primer. Furthermore, it is preferable that the amount of the third primer to be added to the amplification reaction solution is smaller than that of each of the first primer and the second primer.

The third primer to be used herein can be one that allows a starting point for complementary strand synthesis to be provided for a loop portion, with a template having a structure capable of forming the loop, as described in WO02/24902. The third primer, however, is not limited thereto. That is, it can be any primer that provides a starting point for complementary strand synthesis at any site as long as the site is within the target nucleic acid sequence.

The primers included in the primer set according to the present invention each are composed of deoxynucleotides and/or ribonucleotides. In the present invention, "ribonucleotide" (also referred to simply as "N") denotes ribonucleotide triphosphate. Examples thereof include ATP, UTP, CTP, GTP, etc. Furthermore, examples of the ribonucleotide also include derivatives thereof, for instance, ribonucleotide with a sulfur atom substituted for an oxygen atom of a phosphoric acid group in the alpha-position (alpha-thio-ribonucleotide), etc.

In addition, examples of the above-mentioned primers include an oligonucleotide primer that is composed of unmodified deoxynucleotides and/or modified deoxynucleotides, an oligonucleotide primer that is composed of unmodified ribonucleotides and/or modified ribonucleotides, a chimeric oligonucleotide primer that contains unmodified deoxynucleotides and/or modified deoxynucleotides as well as unmodified ribonucleotides and/or modified ribonucleotides, etc.

The primers included in the primer set according to the present invention can be synthesized by any methods that can be used for synthesizing oligonucleotides, for example, a phosphate triesterification method, an H-phosphonate method, a thiophosphonate method, etc. The primers can be obtained easily through the synthesis that is carried out by a phosphoamidite method using a 394 DNA synthesizer manufactured by Applied Biosystem Inc. (ABI), for example.

The template nucleic acid containing a target nucleic acid sequence or the nucleic acid sample that is used for a nucleic acid amplification reaction can be either DNA or RNA. Examples of DNA include all of cDNA, genomic DNA, and synthetic DNA. Examples of RNA include all of whole RNA, mRNA, rRNA, siRNA, hnRNA, and synthetic RNA. These nucleic acids can be prepared from biological samples such as blood, tissues, cells, and further animals and plants, or microorganism samples that have been separated from biological samples, foods, soils, drainage, etc., for example.

The template nucleic acid or nucleic acid sample can be isolated by an arbitrary method. Examples of the method include a dissolution treatment to be carried out using a surfactant, sonication, shaking agitation to be carried out using glass beads, and a method to be carried out using a French press. Furthermore, when an endonuclease is present, it is preferable that an isolated nucleic acid be purified. The nucleic acid can be purified, for example, by phenol extraction, chromatography, ion exchange, gel electrophoresis, density-dependent centrifugation, etc.

More specifically, both a double-stranded nucleic acid, such as PCR fragment or genomic DNA isolated by the above-mentioned methods, and a single-stranded nucleic acid, such as cDNA prepared through a reverse transcription reaction from whole RNA or mRNA, can be used as the template nucleic acid or the nucleic acid sample. In the case of the double-stranded nucleic acid, when it is subjected to denaturing and thereby is allowed to be a single strand, it can be utilized further suitably.

The enzyme to be used for the above-mentioned reverse transcription reaction is not particularly limited, as long as it has a cDNA synthesizing activity utilizing RNA as a template. Examples of the enzyme include reverse transcriptases of diverse origins, such as avian myeloblastosis virus reverse transcriptase (AMV RTase), Rous-associated virus-2 reverse transcriptase (RAV-2 RTase), Moloney murine leukemia virus reverse transcriptase (MMLV RTase), etc. Besides these, a DNA polymerase that additionally has reverse transcription activity also can be used. In order to achieve the object of the present invention, enzymes that have reverse transcription activity at high temperatures are most suitable. For instance, Thermus bacteria derived DNA polymerase (TthDNA polymerase, etc.), Bacillus bacteria derived DNA polymerase, etc. can be used. Examples of particularly preferred enzymes include thermophilic Bacillus bacteria derived DNA polymerases such as B. stearothermophillus derived DNA polymerase (Bst DNA polymerase) and B. caldotenax derived DNA polymerase (Bca DNA polymerase), for example, BcaBEST DNA polymerase, Bca(exo-)DNA polymerase, etc. For instance, the Bca DNA polymerase does not require manganese ions to be used for a (reverse-transcriptase) reaction. The Bca DNA polymerase allows cDNA to be synthesized while preventing the formation of a secondary structure of a template RNA under a high temperature condition.

In the nucleic acid amplification reaction, even when the template nucleic acid is a double-stranded nucleic acid, it can be used for the reaction without further processing. However, it also is possible to denature the double-stranded nucleic acid into a single strand if necessary and then to carry out the annealing of a primer to the template nucleic acid efficiently. Raising the temperature to about 95° C. is a preferred nucleic acid denaturation method. It also is possible to denature the nucleic acid by raising pH, which is considered as another method. In this case, however, it is necessary to lower pH to allow a primer to hybridize to a target nucleic acid.

The polymerase that is used for the nucleic acid amplification reaction can be any polymerase, as long as it has strand displacement activity (strand displacement ability). All of the normal-temperature, mesophilic, and thermostable polymerases can be used suitably. Furthermore, this polymerase can be either a natural product or a variant obtained by artificially varying polymerase. An example of such a polymerase is a DNA polymerase. Preferably, this DNA polymerase has substantially no 5'→3' exonuclease activity. Examples of such a DNA polymerase include: a variant of a DNA polymerase derived from thermophilic Bacillus bacteria, such as Bacillus stearothermophilus (hereinafter referred to as "B. st"), Bacillus caldotenax (hereinafter referred to as "B. ca"), etc., in which the 5'→3' exonuclease activity has been deleted; and a Klenow fragment of E. coli DNA polymerase I. Furthermore, examples of the DNA polymerase to be used for the nucleic acid amplification reaction include Vent DNA polymerase, Vent (Exo-) DNA polymerase, DeepVent DNA polymerase, DeepVent (Exo-) DNA polymerase, phage phi 29 DNA polymerase, MS-2 phage DNA polymerase, Z-Taq DNA polymerase, Pfu DNA polymerase, Pfu turbo DNA polymerase, KOD DNA polymerase, 9° Nm DNA polymerase, Therminater DNA polymerase, etc.

Furthermore, in the nucleic acid amplification reaction described above, when using a DNA polymerase that also has reverse transcription activity, such as BcaBEST DNA polymerase, Bca(exo-) DNA polymerase, etc., the reverse transcription reaction from whole RNA or mRNA and the DNA polymerase reaction that is performed using cDNA as a template can be conducted using one type of polymerase. Moreover, a DNA polymerase and the above-mentioned reverse transcriptase such as the MMLV reverse transcriptase, etc. may be used together in combination.

Examples of the other reagents that can be used for the nucleic acid amplification reaction include: catalysts such as magnesium chloride, magnesium acetate, magnesium sulfate, etc.; a substrate such as a dNTP mix, etc.; and buffer solutions such as a Tris hydrochloride buffer, a Tricine buffer, a sodium phosphate buffer, a potassium phosphate buffer, etc. Furthermore, additives such as dimethyl sulfoxide, betaine (N,N,N-trimethylglycine), etc., acidic materials and cationic complexes described in WO99/54455, etc. also can be used.

In order to improve the nucleic acid amplification efficiency in the nucleic acid amplification reaction, a melting temperature adjusting agent can be added to the reaction solution. The melting temperature (Tm) of a nucleic acid generally is determined by the specific nucleotide sequence of a double-strand forming portion in the nucleic acid. The addition of the melting temperature adjusting agent to the reaction solution allows the melting temperature to be changed. Accordingly, the strength of the double-strand formation in the nucleic acid can be adjusted at a constant temperature. A common melting temperature adjusting agent has an effect of decreasing the melting temperature. When such a melting temperature adjusting agent is added, the melting temperature of the double-strand forming portion located between two nucleic acids can be decreased. In other words, the strength of the double-strand formation can be reduced. Accordingly, in the above-mentioned nucleic acid amplification reaction, the addition of such a melting temperature adjusting agent to the reaction solution allows a double-stranded portion to be a single strand efficiently in a nucleic acid region that is rich in GC for forming a strong double strand and a region where a complicated secondary structure is formed. This makes it easier for the next primer to hybridize to a target region after an extension reaction caused by a primer is completed. Hence, the nucleic acid amplification efficiency can be improved. The melting temperature adjusting agent to be used in the present invention and its concentration in the reaction solution are selected suitably by a person skilled in the art, taking into consideration other reaction conditions that affect the hybridization conditions, for example, salt concentration, reaction temperature, etc. The melting temperature adjusting agent therefore is preferably, but is not particularly limited to, dimethyl sulfoxide (DMSO), betaine, formamide, glycerol, or any combinations thereof, and more preferably dimethyl sulfoxide (DMSO).

Moreover, in the nucleic acid amplification reaction, an enzyme stabilizing agent can be added to the reaction solution. This allows enzymes contained in the reaction solution to be stabilized and thereby the nucleic acid amplification efficiency can be improved. The enzyme stabilizing agent to be used in the present invention can be, but is not particularly limited to, any one of those known in the art, such as glycerol, bovine serum albumin, saccharides, etc.

Furthermore, in the nucleic acid amplification reaction, it also is possible to add, as an enzyme stabilizing agent, a reagent for improving the thermostability of enzymes such as a DNA polymerase, a reverse transcriptase, etc., to the reaction solution. This allows enzymes contained in the reaction solution to be stabilized. Accordingly, the nucleic acid synthesis efficiency and amplification efficiency can be improved. Such a reagent can be any one of those known in the art and is not particularly limited. However, such a reagent is preferably saccharides, more preferably monosaccharides or oligosaccharide, and further preferably trehalose, sorbitol, mannitol, or a mixture of two or more of them.

The nucleic acid amplification reaction to be performed using a primer set according to the present invention can be conducted isothermally. Hence, according to a preferred embodiment of the present invention, this nucleic acid amplification reaction includes: a process of preparing a solution for nucleic acid amplification that contains a template nucleic acid or a nucleic acid sample and a primer set of the present invention; and a process of isothermally incubating the solution for nucleic acid amplification. In this connection, the term "isothermally" denotes that an approximately constant temperature condition is maintained under which enzymes and primers can function suitably. In addition, the expression "an approximately constant temperature condition" denotes not only that the preset temperature is maintained precisely but also that a temperature variation can be tolerated that does not impair the substantial function of enzymes and primers.

A nucleic acid amplification reaction to be performed under a constant temperature condition can be conducted by keeping a temperature at which the activity of enzymes to be used can be maintained. In this nucleic acid amplification reaction, in order for a primer to anneal to a target nucleic acid, for example, the reaction temperature preferably is set at a temperature around the melting temperature (Tm) of the primer or lower. Moreover, it is preferable that the level of stringency be set in consideration of the melting temperature (Tm) of the primer. Accordingly, this temperature is preferably about 20° C. to about 75° C. and more preferably about 35° C. to about 65° C.

In the nucleic acid amplification reaction described above, the amplification reaction is repeated until either the enzyme is inactivated or one of the reagents including the primers is exhausted.

In the above-mentioned nucleic acid amplification reaction, it also is possible to use a nucleic acid containing a non-natural nucleotide, as a template nucleic acid. In the present specification, the term "non-natural nucleotide" denotes a nucleotide that contains a base other than the bases (adenine, guanine, cytosine and thymine or uracil) contained in natural nucleotides and that can be incorporated into a nucleic acid sequence. Examples of the non-natural nucleotide include xanthosines, diaminopyrimidines, isoG, isoC (Proc. Natl. Acad. Sci. USA 92, 6329-6333, 1995), etc. Generally, a nucleic acid amplifying enzyme having no thermostability is used for the amplification of a target nucleic acid that contains a non-natural nucleotide. However, the above-mentioned nucleic acid amplification reaction can be conducted isothermally at, for example, a temperature around 50° C. Hence, the possibility that the nucleic acid amplifying enzyme (a DNA polymerase, etc.) is inactivated is lower as compared with the conventional PCR method. Therefore, the nucleic acid amplification reaction to be performed using the primer set of the present invention also is effective for the amplification of a target nucleic acid containing a non-natural nucleotide, for which a nucleic acid amplifying enzyme having no thermostability is used. The enzyme to be used for the amplification of a nucleic acid containing a non-natural nucleotide is not particularly limited as long as it can amplify such a target nucleic acid. However, particularly from the viewpoint of incorporation efficiency, a Y188L/E478Q mutated HIV I reverse transcriptase, an AMV reverse transcriptase, a Klenow fragment of a DNA polymerase, a 9° N DNA polymerase, a HotTub DNA polymerase, etc. are suitable (Michael Sismour 1 et al., Biochemistry 42, No.28, 8598, 2003/U.S. Pat. No. 6,617,106, Michael J. Lutz et al., Bioorganic & Medical Chemistry letters 8, 1149-1152, 1998, etc.). Furthermore, a substance that improves the thermostability of a nucleic acid amplifying enzyme, for example, trehalose, etc., also can be added to the reaction solution. This makes it possible to amplify a target nucleic acid containing a non-natural nucleotide more efficiently.

The presence of an amplification product obtained by the nucleic acid amplification method according to the present invention can be detected by many various methods. In one method, an amplification product with a specific size is detected by general gel electrophoresis. In this method, it can be detected by using a fluorescent material, such as ethidium bromide, SYBR Green, etc. In another method, an amplification product also can be detected by using a labeled probe that has a label such as biotin and allowing the labeled probe to hybridize to the amplification product. Biotin can be detected by binding to, for instance, fluoresceinated avidin, avidin that has bound to an enzyme such as peroxidase, etc. In still another method, immunochromatograph is employed. In this method, the use of a chromatographic medium in which a macroscopically detectable label is used has been devised (the immunochromatography method). When the above-mentioned amplified fragment and a labeled probe are hybridized to each other and then a capturing probe that can hybridize to another sequence of the amplified fragment is immobilized on the chromatographic medium, the amplified fragment can be trapped by the portion on which the capturing probe has been immobilized. Thus, the detection can be made with the chromatographic medium. As a result, simple detection can be made macroscopically. In the nucleic acid amplification method of the present invention, since the amplification efficiency in the nucleic acid amplification reaction is very high, it also is possible to indirectly detect the amplification product by utilizing the fact that pyrophoric acid is produced as a byproduct of amplification. An example of such a method is a method of visually observing cloudiness of the reaction solution by utilizing the fact that pyrophoric acid binds to magnesium contained in the reaction solution and thereby a white precipitate of magnesium pyrophosphate is produced. Furthermore, another example is a method that utilizes the fact that the magnesium ion concentration in the reaction solution decreases considerably when pyrophoric acid binds strongly to metal ions, such as magnesium, and thereby forms insoluble salt. In this method, when a metallochromic indicator (for example, Eriochrome Black T, Hydroxy Naphthol Blue, etc.) whose color tone changes according to the magnesium ion concentration is added to the reaction solution beforehand, the presence or absence of amplification can be detected by visually observing the change in color of the reaction solution. Moreover, when using Calcein, etc., the increase in intensity of the fluorescence accompanying an amplification reaction can be observed visually. This allows the amplification product to be detected in real time.

According to a preferred embodiment of the present invention, the presence of an amplification product obtained by the nucleic acid amplification method according to the present invention also can be detected by observing the aggregation of a solid-phase support that results from the production of the amplification product. When such detection is to be performed, at least one primer included in the primer set of the present invention has a solid-phase support or a site that can bind to a solid-phase support. The solid-phase support or the site that can bind to a solid-phase support may have been introduced into any portion, such as the 3' end portion, the 5' end portion, or the center region of the primer. However, it is preferable that it has been introduced into the 5' end portion. Furthermore, a substrate to be used for the nucleic acid amplification reaction may contain a solid-phase support or a site that can bind to a solid-phase support.

The solid-phase support to be used in the present invention can be either a support that is insoluble in the reaction solution to be used for the nucleic acid amplification reaction or a phase transition support whose state changes from a liquid phase to a solid phase (gel phase) or from a solid phase (gel phase) to a liquid phase before and after the amplification. Examples of preferred solid-phase support include a water-insoluble organic polymer support, a water-insoluble inorganic polymer support, a synthetic polymer support, a phase transition support, a metal colloid, a magnetic particle, etc. Further examples thereof include a solvent-insoluble organic polymer support, a solvent-insoluble inorganic polymer support, a solvent-soluble polymer support, a gel polymer support, etc. Moreover, examples of the water-insoluble organic polymer include silicon-containing materials such as porous silica, porous glass, diatomaceous earth, sellite, etc., cross-linked polysaccharide such as nitrocellulose, hydroxyapatite, agarose, dextran, cellulose, carboxymethylcellulose, etc., cross-linked protein such as methylated albumin, gelatin, collagen, casein, etc., gel-like particles, dye sol, etc. Examples of the water-insoluble inorganic polymer include aluminum oxide, titanium oxide, ceramic particles, etc. Examples of the synthetic polymer include polystyrene, poly(meth)acrylate, polyvinyl alcohol, polyacrylonitrile, copolymers thereof, a styrene-styrenesulfonic acid copolymer, a vinyl acetate-acrylic ester copolymer, etc. The metal colloid can be a gold colloid, etc. Examples of the magnetic particle include a magnetic iron oxide bead, a monodisperse having pulverized particles of magnetic iron oxide on the surface thereof, a superparamagnetic particle (JP4(1992)-501959A), a magnetically responsive particle having superparamagnetic iron oxide covered with a polymeric silane coating film (JP7 (1995)-6986B), a magnetizable particle of fine powder enclosed in an organic polymer, etc. The magnetized solid-phase support allows a solid and a fluid to be separated easily from each other using magnetic force. Examples of the form of the solid-phase support include a particle, a film, a fiber, a filter, etc. A particularly preferred form of the solid-phase support is a particle whose surface may be either porous or non-porous. Examples of particularly preferred solid-phase supports include latex in which synthetic polymer supports are dispersed uniformly in, for instance, water, metal colloidal particles such as gold colloids, magnetic particles such as magnetic beads, etc.

The immobilization of a primer or a substrate on a solid-phase support can be carried out by a method that is known to a person skilled in the art. The method can use either physical bonds or chemical bonds. The immobilization of a primer or a substrate on a solid-phase support generally can be performed using a combination of a material that can label oligonucleotides of a primer, a probe, etc. and a solid-phase support to which a material that can bind to the above-mentioned material is bound, for example. The combination of materials to be used for such a purpose, those well-known in the art can be used. Examples thereof include a combination of biotin and avidin or streptavidin, a combination of an antigen and an antibody that can bind thereto, a combination of a ligand and a receptor that can bind thereto, a combination of two nucleic acids that hybridize to each other, etc. Specifically, for example, a biotinylated primer or substrate is allowed to bind to a solid-phase support whose surface has been coated with avidin or streptavidin, so that the primer or substrate can be immobilized on the solid-phase support. The antigen can be, for example, hapten, such as FITC, DIG, DNP, etc. while antibodies that can bind thereto are, for example, an anti-FITC antibody, an anti-DIG antibody, an anti-DNP antibody, etc. These antibodies each can be either a monoclonal antibody or a polyclonal antibody. Particularly, biotin and streptavidin bind to each other with high specificity and high binding efficiency. Hence, such a combination is particularly preferable. A labeling material such as biotin, hapten, ligand, etc. can be introduced into the 5' end portion of a primer individually, or if necessary in combination of two or more, by a well-known method (see JP59(1984)-93099A, JP59 (1984)-148798A, and JP59(1984)-204200A).

The site (or group) that can bind to a solid-phase support to be used in the present invention can be selected according to the above-mentioned methods that are used for immobilizing a primer or a substrate on a solid-phase support. Accordingly, the site (or group) can be either one that allows a solid-phase support to bind physically thereto or one that allows a solid-phase support to bind chemically thereto. However, it is preferable that the site (or group) allow a sold-phase support to bind specifically thereto. Examples of such a site that can bind to a solid-phase support include those described above, such as biotin, avidin, streptavidin, an antigen, an antibody, a ligand, a receptor, a nucleic acid, a protein, etc. Such a site is preferably biotin or streptavidin and more preferably biotin. The use of a primer or substrate that contains such a site allows the above-mentioned solid-phase support to bind to an amplification product after the nucleic acid amplification reaction is conducted. The solid-phase support to be used in this case can contain a binding partner for the site that is contained in the primer or substrate, if necessary. Such a binding partner is present in the form that allows it to bind to the site contained in the primer or substrate, preferably is present on the surface of the solid-phase support, and more preferably is one with which the surface of the solid-phase support has been coated.

According to one embodiment of the present invention, a primer set of the present invention is prepared for each of a plurality of target nucleic acids, these plurality of primer sets are immobilized on a solid-phase support in such a manner as to be distinguishable from each other, and then the nucleic acid amplification reaction is conducted using these immobilized primer sets. This makes it possible to amplify a plurality of target nucleic acids simultaneously and to detect amplification products associated with the respective target nucleic acids in the manner that allows them to be distinguished from each other. The amplification products can be detected using, for example, an intercalator. For instance, a plurality of primers are immobilized on a planar solid-phase support at specific positions, respectively, so that after the nucleic acid amplification reaction and the detection of amplification products, amplified target nucleic acids can be specified according to the positions where the amplification products are detected. The solid-phase support that can be used for such a purpose can be not only the above-mentioned planar solid-phase support but also one that is well-known in the art, such as surfaces of beads that are distinguishable from each other (U.S. Pat. Nos. 6,046,807 and 6,057,107), and a sub-planar support that is produced by bundling fibrous supports on which respective primer sets have been solid-phased, which then is cut into thin sections (JP2000-245460A), etc.

The amplified fragment obtained by the nucleic acid amplification method according to the present invention is composed of ordinary bases. Accordingly, it can also be subcloned into a suitable vector by using a restriction enzyme site inside an amplified fragment after amplification. Furthermore, the amplified fragment can also be treated with a restriction enzyme as in RFLP and therefore can widely be used also in the field of genetic test. The above-mentioned amplified fragment can be produced so as to contain a promoter sequence of an RNA polymerase. This allows an RNA to be synthesized directly from the amplified fragment. The RNA thus synthesized also can be used as an RNA probe, siRNA, etc.

In the nucleic acid amplification method according to the present invention, a base that has been labeled with biotin or a fluorescent material can be used as a substrate instead of ordinary dNTP. This allows a DNA probe labeled with biotin or a fluorescent material to be prepared. Furthermore, it also is possible to determine the presence or absence of an amplification product through a certain structure of the biotin, labeling material, etc.

A primer that is included in the primer set of the present invention is allowed to contain a restriction enzyme recognition site. This makes it possible to improve the nucleic acid amplification efficiency. That is, a nick is caused in an amplification product by a restriction enzyme corresponding to the restriction enzyme recognition site contained in the primer. Hence, it is possible to cause a complementary strand synthesis reaction of a strand displacement type, with the nick being used as a synthesis starting point. Basically, this method is based on the principle of the SDA method described as prior art. In the present invention, however, this method is different therefrom in that the nucleic acid to serve as a template has a structure in which nucleic acids complementary to each other are joined alternately to each other as shown in FIGS. 3(m) and 3(o). In this method, it is necessary to design the primer so that a dNTP derivative is incorporated into a portion to be a complementary strand to a reverse primer to be nicked, so as to provide the portion with nuclease resistance so that the double strand is prevented from being cleaved by the restriction enzyme.

A primer that is included in the primer set according to the present invention can contain a promoter sequence of an RNA polymerase. This allows the nucleic acid amplification efficiency to be improved. Basically, this method is based on the principle of the NASBA method described as a prior art. In the present invention, however, since transcription from a long-chain amplification product as shown in FIG. 3(m) is made by the RNA polymerase that recognizes the promoter, the primer can bind easily to a single-stranded RNA that is a transcription product. Thus, the amplification efficiency can be improved.

Furthermore, the primer set according to the present invention can include an "outer primer" that is used in the LAMP method or the SDA method. This makes it possible to improve the nucleic acid amplification efficiency. The outer primer to be used herein can be a primer that allows a portion located on the outer side of a target nucleic acid sequence on a template nucleic acid to be provided with a starting point for complementary strand synthesis.

The nucleic acid amplification method according to the present invention makes it possible to produce the following easily and quickly: a single-stranded nucleic acid to be immobilized on a DNA chip, a single-stranded DNA probe to be used for determining a base sequence, a megaprimer to be used for a long-chain PCR method, etc. Furthermore, the nucleic acid amplification method according to the present invention also makes it possible to selectively amplify only a sense sequence or only an antisense sequence of a target nucleic acid according to the purpose.

A single-stranded nucleic acid prepared by the nucleic acid amplification method of the present invention can be used as a DNA fragment to be immobilized on a DNA chip. That is, the nucleic acid amplification method of the present invention also is applicable to a method of preparing a DNA strand to be immobilized in a process of producing a DNA chip. Furthermore, it also is possible to produce a DNA chip by immobilizing the 5' end of a primer on the DNA chip beforehand and then performing the nucleic acid amplification on the chip. When a fluoresceinated probe that hybridizes to an amplification product is added to a reaction solution before the nucleic acid amplification is carried out, an amplification product can be detected in real time while the nucleic acid amplification is performed on the DNA chip.

It is possible to determine the presence or absence of a mutation in a nucleic acid sequence contained in a nucleic acid sample by utilizing the nucleic acid amplification reaction to be performed using the primer set according to the present invention. For this purpose, the primer set can be designed so that a mutation site is contained in the aforementioned sequence (A), sequence (B), or sequence (C). This allows the presence or absence of the mutation to be determined by checking the presence or absence of an amplification product. Hence, the present invention provides a method of determining the presence or absence of a mutation in a nucleic acid sequence contained in a nucleic acid sample. The method includes: (a) a process of preparing a nucleic acid sample; (b) a process of preparing a primer set according to the present invention that is designed so that a nucleic acid sequence with or without the mutation serves as a target nucleic acid sequence, and a nucleotide residue associated with the mutation is contained in a sequence (A), a sequence (B), or a sequence (C); and (c) a process of performing a nucleic acid amplification reaction in the presence of the nucleic acid sample using the primer set.

In the mutation detection method of the present invention, when using a primer set that is designed so that a nucleic acid sequence containing a target mutation serves as a target nucleic acid sequence, the presence of an amplification product after the nucleic acid amplification reaction indicates the presence of the mutation, while the absence of or reduction in the amplification product indicates the absence of the mutation. On the other hand, when using a primer set that is designed so that a nucleic acid sequence containing no target mutation serves as a target nucleic acid sequence, the presence of an amplification product after the nucleic acid amplification reaction indicates the absence of the mutation, while the absence of or reduction in the amplification product indicates the presence of the mutation. In this case, the expression "reduction in the amplification product" denotes a reduction in amount of the amplification product obtained as compared to the amount of the amplification product that is obtained when the target nucleic acid sequence is present in the nucleic acid sample.

In the present invention, the term "mutation" denotes that a base (a base pair in the case of a double-stranded nucleic acid) that is different from that contained in a control nucleic acid sequence is present in the nucleic acid sequence. In the present invention, the term "control nucleic acid" denotes a nucleic acid that has a wild-type (also referred to as a "normal-type") sequence that is considered as a standard base sequence, for example, a standard genotype, with respect to a certain specific base sequence. On the other hand, the term "test nucleic acid" means a nucleic acid to be tested for the presence or absence of a base (mutation) that is different from that contained in a control nucleic acid in the mutation detection method of the present invention. In other words, it means a nucleic acid that is present in a nucleic acid sample and has an identical sequence to that of the control nucleic acid except for the base associated with the mutation. Furthermore, in the present invention, the expression "base associated with a mutation" or "nucleotide residue associated with a mutation" denotes a base or a nucleotide residue that is present at the mutation site in a nucleic acid. It therefore denotes both the base or nucleotide residue that is contained at the mutation site in a control nucleic acid and the base or nucleotide residue that is contained at the mutation site in a mutated-type nucleic acid. For example, in the case of detecting a mutation in a gene of a patient suspected of having a genetic disease, the gene of the patient suspected of having a mutation is a test nucleic acid. On the other hand, a gene of a healthy subject corresponding to the gene of the patient is a control nucleic acid.

The above-mentioned test nucleic acid and control nucleic acid may be either a natural product-derived nucleic acid or an artificially synthesized nucleic acid. The term "nucleic acid" to be used in the present invention means a polynucleotide containing any unmodified nucleotide and/or modified nucleotide. Typically, the test nucleic acid and control nucleic acid each are DNA such as cDNA, genomic DNA, synthetic DNA, etc. or RNA such as mRNA, whole RNA, hnRNA, siRNA, synthetic RNA, etc. Furthermore, the term "polynucleotide" to be used in the present invention encompasses polynucleotides and oligonucleotides as well as artificially synthesized nucleic acids such as peptide nucleic acid, morpholino nucleic acid, methylphosphonate nucleic acid, and S-oligo nucleic acid, etc., for convenience. A tester can select a test nucleic acid and a control nucleic acid arbitrarily. These nucleic acids may be in the intermingled state during detection.

According to one embodiment of the present invention, in the process (b) of the mutation detection method according to the present invention, a primer set is prepared that is designed so that the nucleotide residue associated with the mutation is contained in the sequence (A). In this embodiment, when the target nucleic acid sequence is contained in the nucleic acid sample, the first primer anneals to the sequence (A) in the nucleic acid amplification reaction and thereby an amplification product is obtained. On the other hand, when a nucleic acid sequence that is different in mutation site from the target nucleic acid sequence is contained in the nucleic acid sample, it is difficult for the first primer to anneal to the sequence (A) in the nucleic acid amplification reaction. Hence, in this case, no amplification product is obtained or a considerably reduced amount of amplification product is obtained. Preferably, the nucleotide residue associated with the mutation is contained in the 5' end (corresponding to the 3' end of the first primer) of the sequence (A). Furthermore, it is preferable that the sequence (Ac') contained in the first primer be a sequence that is complementary to the sequence (A).

According to another embodiment of the present invention, in the process (b) of the mutation detection method according to the present invention, a primer set is prepared that is designed so that the nucleotide residue associated with the mutation is contained in the sequence (C). In this embodiment, when the target nucleic acid sequence is contained in the nucleic acid sample, the second primer anneals to the sequence (C) in the nucleic acid amplification reaction and thereby an amplification product is obtained. On the other hand, when a nucleic acid sequence that is different in mutation site from the target nucleic acid sequence is contained in the nucleic acid sample, it is difficult for the second primer to anneal to the sequence (C) in the nucleic acid amplification reaction. Hence, in this case, no amplification product is obtained or a considerably reduced amount of amplification product is obtained. Preferably, the nucleotide residue associated with the mutation is contained in the 5' end (corresponding to the 3' end of the second primer) of the sequence (C). Furthermore, it is preferable that the sequence (Cc') contained in the second primer be a sequence that is complementary to the sequence (C).

According to another embodiment of the present invention, in the process (b) of the mutation detection method according to the present invention, a primer set is prepared that is designed so that the nucleotide residue associated with the mutation is contained in the sequence (B). In this embodiment, when the target nucleic acid sequence is contained in the nucleic acid sample, after the first primer anneals to the sequence (A) to cause an extension reaction, a sequence (B') that is contained in the primer hybridizes to a sequence (Bc) on the extended strand and thereby a stem-loop structure is formed efficiently in the nucleic acid amplification reaction. This efficient formation of the stem-loop structure allows another first primer to anneal to the template. Accordingly, the action mechanism shown in FIG. 1 proceeds efficiently and thereby an amplification product is obtained. On the other hand, when a nucleic acid sequence that is different in mutation site from the target nucleic acid sequence is contained in the nucleic acid sample, it is difficult to form the above-mentioned stem-loop structure in the nucleic acid amplification reaction. Thus, the action mechanism shown in FIG. 1 is hindered. As a result, no amplification product is obtained or a considerably reduced amount of amplification product is obtained. Preferably, the sequence (B') contained in the first primer is a sequence identical to the sequence (B).

The detection of the mutation in the above-mentioned sequence (B) is described further in detail. In the action mechanism shown in FIG. 1, the phenomenon in which the sequence (B') hybridizes to the sequence (Bc) occurs due to the presence of complementary regions on the same strand. Generally, when a double-stranded nucleic acid dissociates into a single strand, partial dissociation starts from its ends or relatively unstable portions other than the ends. In the double-stranded nucleic acid produced through the extension reaction caused by the first primer, the base pairs located in the end portion are in a state of equilibrium between dissociation and binding at relatively high temperatures and thereby a double strand is retained as a whole. In such a state, when a sequence complementary to the dissociated portion located at the end is present on the same strand, a stem-loop structure can be formed in a metastable state. However, this stem-loop structure does not exist stably. Particularly, when a noncomplementary nucleotide is present between the sequence (B') and sequence (Bc) portions that form the stem, the stem-loop structure is very unstable or the stem is not formed at all. In this case, the hybridization between the sequence (A) on the template and the sequence (Ac') in the primer become dominant. Hence, the sequence (A) portion does not dissociate into a single strand and therefore the next first primer cannot anneal. Accordingly, it becomes very difficult to cause the continuous reaction shown in FIG. 1 The nucleic acid sample containing a test nucleic acid can be obtained from a test body, for example, a human being or a nonhuman animal. In this case, nucleic acids can be extracted from samples, such as desired tissues, organs, cells, etc. obtained from the test body, by a method known in the art. It also is possible to adjust the conditions such as the size and the purity after purification of a nucleic acid fragment, into adequate conditions after the extraction, if necessary. Thereafter, further an amplification reaction may be performed through, for example, a general polymerase chain reaction (PCR), and thereby the test nucleic acid contained in the nucleic acid sample may be amplified.

The test nucleic acid and control nucleic acid each may be a single strand or may be a double strand. The term "double-stranded nucleic acid" that is used in the present invention denotes any of double-stranded DNA, double-stranded RNA, and DNA/RNA. The double-stranded nucleic acid may be used as a nucleic acid sample without further processing, or may be used after being amplified with a vector, such as phage or plasmid.

According to a preferred embodiment of the present invention, the nucleic acid amplification reaction in the mutation detection method according to the present invention is conducted in the presence of a mismatch recognition protein. This allows the mutation to be detected more accurately.

It has been known already that in the case where a base pair that cannot be paired (mismatch) is produced partly in a double strand of a DNA, bacteria, yeast, etc. have mechanisms for repairing it. This repair is performed by a protein called a "mismatch binding protein" (also referred to as a "mismatch recognition protein"). The use of various mismatch binding proteins, such as MutS protein (JP9(1997)-504699A), MutM protein (JP2000-300265A), MutS protein that has bound to a green fluorescence protein (GFP) (WO99/06591), etc. has been reported. Furthermore, recently, a gene diagnostic method has been developed in which a mismatch is detected using a mismatch binding protein (M. Gotoh et al., Genet. Anal., 14, 47-50, 1997). The following method of detecting a mismatch has been known as a method of detecting a polymorphism and a mutation in a specific nucleotide contained in a nucleic acid. That is, for example, a control nucleic acid containing no mutation and a test nucleic acid that is suspected of containing a mutation present therein are hybridized to each other and then a mismatch recognition protein is introduced thereinto to detect a mismatch.

In the present invention, the term "mismatch" means that a base pair selected from adenine (A), guanine (G), cytosine (C), and thymine (T) (uracil (U) in the case of RNA) is not a normal base pair (a pair of A and T, or a pair of G and C). The "mismatch" denotes not only one mismatch but also a plurality of consecutive mismatches, mismatches that occur due to an insertion and/or deletion of one base or a plurality of bases, and combinations thereof.

In the mutation detection method according to the present invention, the specificity (accuracy) can be improved by using such a mismatch binding protein. In the mutation detection method of the present invention, when the test nucleic acid contained in the nucleic acid sample has a different nucleotide from that of the target nucleic acid sequence at the mutation site, the sequence (Ac') contained in the first primer or the sequence (Cc') contained in the second primer is hindered from hybridizing to the test nucleic acid, or the stem-loop structure is hindered from being formed of the sequence (B') contained in the first primer. Thus no amplification product is obtained or a reduced amount of amplification product is obtained. However, such hybridization or formation of the stem-loop structure may not be hindered completely in some cases. In such cases, a small amount of heteroduplex structures are formed in these sequences. In the present invention, the term "heteroduplex structure" denotes substantially a complementary duplex structure. However, it also means a duplex structure containing a noncomplementary region due to one or a plurality of mismatches contained therein. Such a heteroduplex structure results in a false amplification product that should not be produced normally. Thus, when a mismatch binding protein has been added to the reaction solution to be used for the nucleic acid amplification reaction, this mismatch binding protein binds to such a heteroduplex structure as described above, which prevents the amplification reaction from occurring thereafter. Accordingly, production of a false amplification product can be prevented by using the mismatch binding protein.

The mismatch binding protein to be used in the present invention can be any protein that recognizes a mismatch in a double-stranded nucleic acid and can bind to the mismatch site. It can be any one of proteins that are well-known to a person skilled in the art, for example. In addition, the mismatch binding protein to be used in the present invention may be a protein (mutant) that consists of an amino acid sequence that is obtained through the replacement, deletion, addition, and/or insertion of one or a plurality of amino acids in an amino acid sequence of a wild-type protein, as long as it can recognize a mismatch in the double-stranded nucleic acid. Such a mutant may be produced in nature but it also can be produced artificially. Many methods have been known as a method of introducing an amino acid mutation into a protein. For example, the method of W. P. Deng and J. A. Nickoloff (Anal. Biochem., 200, 81, 1992), the method of K. L. Makamaye and F. Eckstein (Nucleic Adids Res., 14, 9679-9698, 1986), etc. have been known as site-specific mutagenesis. Furthermore, the method of using the E. coli XL1-Red strain (Stratagene, Inc.) that is deficient in the basic repair system, the method of chemically modifying a base using sodium nitrite, for example (J.-J. Diaz et al., BioTechnique, 11, 204-211, 1991), etc. have been known as random mutagenesis. Many mismatch binding proteins have been know including MutM, MutS, analogs thereof, etc. (Radman, M. et al., Annu. Rev. Genet. 20:523-538 (1986); Radaman, M. et al., Sci. Amer., August 1988, pp40-46; Modrich, P., J. Biol. Chem. 264:6597-6600 (1989); Lahue, R. S. et al., Science 245:160-164 (1988); Jiricny, J. et al,. Nucl. Acids Res. 16:7843-7853 (1988); Su, S. S. et al., J. Biol. Chem. 263;6829-6835 (1988); Lahue, R. S. et al., Mutat. Res. 198:37-43 (1988); Dohet, C. et al., Mol. Gen. Gent. 206:181-184 (1987); Jones, M. et al., Gentics 115:605-610 (1987); Muts of Salmonella typhimurium (Lu, A. L., Genetics 118:593-600 (1988); Haber L. T. et al., J. Bacteriol. 170:197-202(1988); Pang, P. P. et al., J. Bacteriol. 163:1007-1015 (1985); and Priebe S. D. et al., J. Bacteriol. 170:190-196 (1988)). The mismatch binding protein to be used in the present invention is preferably MutS, MutH, MutL, or one derived from yeast, and is more preferably MutS, MutH, or MutL.

It has been known that a mismatch binding protein also may bind to a single-stranded nucleic acid, and such binding of a mismatch binding protein to a single-stranded nucleic acid is inhibited by a single-stranded nucleic acid binding protein. Hence, when a mismatch binding protein is used in the mutation detection method of the present invention, it is preferable that a single-stranded nucleic acid binding protein be used together. Furthermore, it also has been known that a mismatch binding protein also may bind to a double-stranded nucleic acid containing no mismatch, and such improper binding of a mismatch binding protein can be inhibited when the mismatch binding protein is activated using an activator beforehand. Accordingly, when using a mismatch binding protein in the mutation detection method of the present invention, it is preferable to use one that has been activated with an activator beforehand.

The single-stranded nucleic acid binding protein (SSB) to be used to inhibit a mismatch binding protein from binding to a single-stranded nucleic acid can be any SSB that is well-known in the art. Examples of preferred SSB include Escherichia coli, Drosophila, a single-stranded nucleic acid binding protein from Xenopus laevis, T4 Bacteriophage gene 32 protein, and equivalents thereof that are derived from other species. Examples of the mismatch binding protein to be used in this case include MutS, MutH, MutL, HexA, MSH 1-6, Rep3, RNaseA, uracil-DNA glycosidase, T4 endonuclease VII, resolvase, etc. The mismatch binding protein is preferably MutS, MSH2, MSH6, or a mixture of two or more of them, and is more preferably MutS.

The activator to be used for activating a mismatch binding protein can be selected suitably by a person skilled in the art and therefore is not particularly limited. It, however, is preferably a compound such as ATP (adenosine 5'-triphosphate), ADP (adenosine 5'-diphosphate), ATP-gamma-S(adenosine 5'-O-(3-thiotriphosphate)), AMP-PNP (adenosine 5'-[beta, gamma-imide]triphosphate), etc. or one of nucleotides that can bind to a mismatch binding protein. A mismatch binding protein can be activated by incubating the mismatch binding protein and an activator at room temperature for several seconds to several minutes.

According to a preferred embodiment of the present invention, the mutation detection method according to the present invention can be used to check whether a specific gene has a mutation, in a test body that is suspected of being suffered from a gene disease, or to check whether a gene of a patient and a gene of a healthy person have the same base sequence. In the mutation detection method according to the present invention, it is possible to detect any mutations regardless of their positions in a test gene.

Furthermore, according to the nucleic acid amplification reaction to be performed using a primer set according to the present invention, it is possible to determine the presence or absence of a deletion or insertion of a sequence in a nucleic acid sequence contained in a nucleic acid sample. For this purpose, the primer set can be designed so that the site associated with a deletion or insertion is contained in the sequence (A), sequence (B), or sequence (C), or is positioned between the sequence (A) and the sequence (B) or between the sequence (A) and the sequence (C). This makes it possible to determine the presence or absence of a deletion or insertion of a sequence by checking the presence or absence of an amplification product. Hence, the present invention provides a method of determining the presence or absence of a deletion or insertion of a sequence in a nucleic acid sequence contained in a nucleic acid sample. The method includes: (a) a process of preparing a nucleic acid sample; (b) a process of preparing a primer set according to the present invention that is designed so that a nucleic acid sequence with or without a sequence associated with a deletion or insertion serves as a target nucleic acid sequence, and a site associated with the deletion or insertion is contained in the sequence (A), sequence (B), or sequence (C), or is positioned between the sequence (A) and the sequence (B) or between the sequence (A) and the sequence (C); and (c) a process of performing a nucleic acid amplification reaction in the presence of the nucleic acid sample using the primer set.

In the deletion/insertion determination method of the present invention, when using a primer set that is designed so that a nucleic acid sequence containing a sequence associated with an aimed deletion or insertion serves as a target nucleic acid sequence, the presence of an amplification product after the nucleic acid amplification reaction indicates the presence of the sequence associated with the deletion or insertion, while the absence of or reduction in the amplification product indicates the absence of the sequence associated with the deletion or insertion. On the other hand, when using a primer set that is designed so that a nucleic acid sequence containing no sequence associated with the aimed deletion or insertion serves as a target nucleic acid sequence, the presence of an amplification product after the nucleic acid amplification reaction indicates the absence of the sequence associated with the deletion or insertion, while the absence of or reduction in the amplification product indicates the presence of the sequence associated with the deletion or insertion. In this case, the expression "reduction in the amplification product" denotes a reduction in amount of the amplification product obtained as compared to the amount of the amplification product that is obtained when the target nucleic acid sequence is present in the nucleic acid sample.

According to one embodiment of the present invention, in the process (b) of the deletion/insertion determination method according to the present invention, a primer set is prepared that is designed so that the site associated with the deletion or insertion is contained in the sequence (A). In this embodiment, when the target nucleic acid sequence is contained in the nucleic acid sample, the first primer anneals to the sequence (A) in the nucleic acid amplification reaction and thereby an amplification product is obtained. On the other hand, when a nucleic acid sequence that is different from the target nucleic acid sequence due to the deletion or insertion is contained in the nucleic acid sample, it is difficult for the first primer to anneal to the sequence (A) in the nucleic acid amplification reaction. Hence, in this case, no amplification product is obtained or a considerably reduced amount of amplification product is obtained. Preferably, the sequence (Ac') contained in the first primer is a sequence that is complementary to the sequence (A).

According to another embodiment of the present invention, in the process (b) of the deletion/insertion determination method according to the present invention, a primer set is prepared that is designed so that the site associated with the deletion or insertion is contained in the sequence (C). In this embodiment, when the target nucleic acid sequence is contained in the nucleic acid sample, the second primer anneals to the sequence (C) in the nucleic acid amplification reaction and thereby an amplification product is obtained. On the other hand, when a nucleic acid sequence that is different from the target nucleic acid sequence due to the deletion or insertion is contained in the nucleic acid sample, it is difficult for the second primer to anneal to the sequence (C) in the nucleic acid amplification reaction. Hence, in this case, no amplification product is obtained or a considerably reduced amount of amplification product is obtained. Preferably, the sequence (Cc') contained in the second primer is a sequence that is complementary to the sequence (C).

According to another embodiment of the present invention, in the process (b) of the deletion/insertion determination method according to the present invention, a primer set is prepared that is designed so that the site associated with the deletion or insertion is contained in the sequence (B). In this embodiment, when the target nucleic acid sequence is contained in the nucleic acid sample, after the first primer anneals to the sequence (A) to cause an extension reaction, a sequence (B') that is contained in the primer hybridizes to a sequence (Bc) located on the extended strand and thereby a stem-loop structure is formed efficiently in the nucleic acid amplification reaction. This efficient formation of the stem-loop structure allows another first primer to anneal to the template. Accordingly, the action mechanism shown in FIG. 1 proceeds efficiently and thereby an amplification product is obtained. On the other hand, when a nucleic acid sequence that is different from the target nucleic acid sequence due to the deletion or insertion is contained in the nucleic acid sample, it is difficult to form the above-mentioned stem-loop structure in the nucleic acid amplification reaction. Thus, the action mechanism shown in FIG. 1 is hindered. As a result, no amplification product is obtained or a considerably reduced amount of amplification product is obtained. The details are as described above with respect to the mutation detection method of the present invention. Preferably, the sequence (B') contained in the first primer is a sequence identical to the sequence (B).

According to a preferred embodiment of the present invention, in the process (b) of the deletion/insertion determination method according to the present invention, a primer set is prepared that is designed so that the site associated with the deletion or insertion is positioned between the sequence (A) and the sequence (B). In this embodiment, when the target nucleic acid sequence is contained in the nucleic acid sample, after the first primer anneals to the sequence (A) to cause an extension reaction, the sequence (B') that is contained in the primer hybridizes to the sequence (Bc) located on the extended strand and thereby a stem-loop structure is formed efficiently in the nucleic acid amplification reaction. This efficient formation of the stem-loop structure allows another first primer to anneal to the template. Accordingly, the action mechanism shown in FIG. 1 proceeds efficiently and thereby an amplification product is obtained. On the other hand, when a nucleic acid sequence that is different from the target nucleic acid sequence due to the deletion or insertion is contained in the nucleic acid sample, it is difficult to form the above-mentioned stem-loop structure in the nucleic acid amplification reaction since the distance maintained between the sequence (B') that is contained in the first primer and the sequence (Bc) located on the extended strand is not adequate. Thus, in this case, the action mechanism shown in FIG. 1 is hindered. As a result, no amplification product is obtained or a considerably reduced amount of amplification product is obtained.

According to another embodiment of the present invention, in the process (b) of the deletion/insertion determination method according to the present invention, a primer set is prepared that is designed so that the site associated with the deletion or insertion is positioned between the sequence (A) and the sequence (C). In this embodiment, when the target nucleic acid sequence is contained in the nucleic acid sample, after the first primer anneals to the sequence (A) to cause an extension reaction, the sequence (B') that is contained in the primer hybridizes to the sequence (Bc) located on the extended strand and thereby a stem-loop structure is formed efficiently in the nucleic acid amplification reaction. This efficient formation of the stem-loop structure allows another first primer to anneal to the template. Accordingly, the action mechanism shown in FIG. 1 proceeds efficiently and thereby an amplification product is obtained. On the other hand, when a nucleic acid sequence that is different from the target nucleic acid sequence due to the deletion or insertion is contained in the nucleic acid sample, no amplification product is obtained or a considerably reduced amount of amplification product is obtained. For instance, when the nucleic acid sample contains a nucleic acid sequence that is different from the target nucleic acid sequence due to the insertion of a long sequence between the sequence (A) and the sequence (C), the rate (efficiency) of nucleic acid amplification decreases considerably. As a result, no amplification product is obtained or a considerably reduced amount of amplification product is obtained. Furthermore, when the nucleic acid sample contains a nucleic acid sequence that is different from the target nucleic acid sequence due to the deletion of a sequence between the sequence (A) and the sequence (C) and when a part or the whole of the sequence (B) has been lost due to the deletion, the sequence (B') contained in the first primer cannot hybridize onto the extended strand. Accordingly, a stem-loop structure cannot be formed or is difficult to form. Thus, the action mechanism shown in FIG. 1 is hindered. As a result, no amplification product is obtained or a considerably reduced amount of amplification product is obtained. Moreover, when the nucleic acid sample contains a nucleic acid sequence that is different from the target nucleic acid sequence due to the deletion of a sequence between the sequence (A) and the sequence (C) and even when no partial deletion of the sequence (B) is caused by the deletion, the rate (efficiency) of nucleic acid amplification decreases. As a result, no amplification product is obtained or a considerably reduced amount of amplification product is obtained.

In the deletion/insertion determination method of the present invention, DNA and RNA each can be used as a target nucleic acid sequence. Examples of RNA include mRNA, spliced RNA, unspliced RNA as well as all kinds of RNAs that can be obtained from biological bodies, such as RNAs that exist in nuclei, cytoplasm, etc., RNAs derived from infected viruses, bacteria, etc. Examples of DNA include not only natural DNAs but also artificially recombined DNA sequences. Currently, recombination of sequences of various genes or nucleic acid fragments has been made possible. According to the deletion/insertion determination method of the present invention, it also is possible to detect non-natural recombinant sequences.

According to a preferred embodiment of the present invention, the sequence associated with the above-mentioned deletion or insertion is an intronic sequence that is contained in a gene on a genome of a eukaryote. In this case, when using a nucleic acid sample containing both mRNA and genomic DNA, it can be determined whether the intron is present in a sequence of a target gene. As a result, when the intron is judged to be absent, it can be determined that mRNA of the target gene is present, that is, the target gene has been expressed. According to a further preferred embodiment of the present invention, the target nucleic acid sequence is mRNA.

The following detailed description is made with respect to an embodiment in which a primer set is used that is designed so that mRNA (with an intron having been deleted) of the target gene serves as a target nucleic acid sequence, and the site associated with the deletion of the intronic sequence is positioned between the sequence (A) and the sequence (B). In this embodiment, first, the sequence (Ac') that is present at the 3'end of the first primer anneals to the template to cause an extension reaction. Further, only when a target region has been synthesized in the product obtained by the extension reaction caused by the primer, can the sequence (B') that is present at the 5' end of the primer hybridize to the sequence (Bc) corresponding to exon located next thereto on a self-extension product. That is, it is not until the target region of mRNA having a sequence with two exons joined sequentially is synthesized in the extension reaction product that the stem-loop structure shown in FIG. 1 is formed, which allows a new first primer to anneal to the sequence (A) located on the template that has become a single strand. As described above, the formation of the stem-loop structure by the 5' end portion of this first primer is repeated efficiently when the sequence (A) and the sequence (B) located on the template exist at a suitable interval. Accordingly, when only using mRNA containing no intronic sequence as a template, amplification occurs, while no amplification occurs in genomic DNA that contains an intronic sequence. When this reaction is repeated isothermally, the target nucleic acid can be amplified accurately and the formation of the stem-loop structure is repeated accurately for every cycle. Thus the target nucleic acid alone can be amplified accurately. For example, in the PCR method, since nonspecific amplification occurs in many cases, it is very difficult to amplify a target mRNA alone and quantitatively determine it. However, since the deletion/insertion determination method of the present invention has very high specificity, nonspecific amplification does not occur and thereby the target mRNA alone can be amplified specifically, which also improves the quantitativity thereof. Furthermore, this principle makes it possible to omit a process of obtaining RNA by a complicated, time-consuming DNase treatment to decompose DNA contained in a test sample. Hence, spontaneous decay of mRNA can be reduced and thereby quicker qualitative or quantitative diagnosis can be conducted.

In order to carry out the nucleic acid amplification method, mutation detection method, or deletion/insertion determination method according to the present invention, necessary reagents can be put together into a kit. Accordingly, a kit of the present invention includes a primer set of the present invention. The nucleic acid amplification method, mutation detection method, or deletion/insertion determination method according to the present invention has an advantage in requiring no primers other than those included in the primer set according to the present invention. Hence, according to a preferred embodiment of the present invention, the kit of the present invention does not include any primer components other than those included in the primer set of the present invention. When at least one primer included in the primer set of the present invention contains a site that can bind to a solid-phase support, it is preferable that the kit of the present invention further include the solid-phase support. Similarly in the case where the substrate to be used for the nucleic acid amplification reaction contains a site that can bind to a solid-phase support, it is preferable that the kit of the present invention further include the solid-phase support. The kit of the present invention further may include the above-mentioned reagents such as DNA polymerase, dNTP, a buffer solution, etc., a reaction vessel, an instruction manual, etc.

According to a preferred embodiment of the present invention, the above-mentioned kit includes a primer set according to the present invention and a reaction vessel containing other reagents that are necessary for the nucleic acid amplification reaction. Examples of other reagents include the aforementioned reagents such as a DNA polymerase, dNTP, a buffer solution, etc. The use of such a kit makes it possible to perform the nucleic acid amplification reaction merely by adding a template nucleic acid or a nucleic acid sample into the reaction vessel and maintaining the reaction vessel at a constant temperature. When at least one primer included in the primer set contains a solid-phase support, the solid-phase support aggregates at the same time as an amplification product is produced. Accordingly, when using a transparent or translucent reaction vessel, this aggregation can be observed from the outside of the reaction vessel. Hence, in this case, the amplification product can be detected without opening the reaction vessel. Thus, the operation is simple and easy and in addition, the nucleic acid amplification product is prevented from being contaminated with other samples.

A second aspect of the present invention provides a method of determining the presence or absence of a mutation in a nucleic acid sequence contained in a nucleic acid sample by performing a nucleic acid amplification reaction using a nucleic acid reagent that causes a mismatch with a template depending on the presence or absence of a mutation in the template, in the presence of a substance having mismatch recognition ability such as a mismatch binding protein. The term "mutation" that is used in this aspect encompasses all the substitution, deletion, and insertion of at least one nucleotide.

In the present specification, the "substance having mismatch recognition ability" denotes a substance that binds to a mismatch site or cleaves the site when a mismatch is contained in a double-stranded nucleic acid. In the nucleic acid amplification reaction to be performed using a primer and DNA polymerase, if a double-stranded region exists in which a substance having mismatch recognition ability has bound onto a target nucleic acid sequence in a template, the double-stranded structure is not decomposed even when a strand extended from the primer reaches there. Accordingly, the primer extension reaction stops there and thus no amplification product can be obtained. Similarly, when the target nucleic acid sequence contained in the template is cleaved in the nucleic acid amplification reaction, no amplification product can be obtained. The substance having mismatch recognition ability is preferably a substance that binds to a mismatch portion. The substance can be an organic compound, an inorganic compound, a protein, or a complex thereof but particularly preferably is a mismatch binding protein that binds to a mismatch portion. Although the details of the mismatch binding protein are as described above, the mismatch binding protein is preferably MutS, MSH2, MSH6, or a mixture of two or more of them and is more preferably MutS (J Smith and P Modrich, Proc. Natl. Acad. Sci. USA. 93, 4374-4379, 1996; Au K G, Welsh K, Modrich P., J. Biol. Chem. 267, 12142-12148, 1992; and Alan B. Clark, Frank Valle, Karin Drotschmann, Ronald K. Gary, and Thomas A. Kunkel, J. Biol. Chem. 275, 36498-36501, 2000). The mismatch binding protein varies in thermostability, depending on the biological body of its origin. Any person skilled in the art can select a suitable mismatch binding protein according to the temperature to be set in the nucleic acid amplification reaction. For example, MutS derived from thermophilic bacterium can be used suitably in the present invention.

The above-mentioned nucleic acid amplification reaction may be performed by any method well-known in the art, or may be performed by the nucleic acid amplification method according to the present invention. Particularly, a nucleic acid amplification reaction that is conducted isothermally is used suitably. Such a nucleic acid amplification reaction can be performed not only by the above-mentioned nucleic acid amplification method of the present invention but also by a method that is known as a nucleic acid amplification method to be carried out isothermally, for example, the SDA method (JP7(1995)-114718B), the improved SDA method (U.S. Pat. No. 5,824,517, WO99/09211, WO95/25180), the NASBA method (Japanese Patent No. 2650159), the LAMP method (WO/0028082), the ICAN method (WO02/16639), etc.

According to one embodiment, the mutation detection method of the second aspect of the present invention includes the following processes:

(a) a process of preparing a nucleic acid sample;
(b) a process of preparing a primer set that allows a target nucleic acid sequence containing a site associated with a mutation to be amplified, wherein the primer set is designed so that when at least one primer included in the primer set hybridizes to a nucleic acid sequence contained in the nucleic acid sample or the complementary sequence thereto, at least one mismatch occurs between the primer and the nucleic acid sequence or the complementary sequence thereto, depending on the presence or absence of the mutation; and
(c) a process of performing a nucleic acid amplification reaction in the presence of a substance having mismatch recognition ability, using the primer set in which the nucleic acid sample serves as a template.

The above-mentioned primer set that allows a target nucleic acid sequence to be amplified can be designed suitably according to the nucleic acid amplification method to be employed. Particularly, it is preferable that the primer set allow the target nucleic acid sequence to be amplified isothermally. In that case, the nucleic acid amplification reaction can be performed isothermally.

The at least one mismatch described above can be a mismatch of one base, a plurality of consecutive mismatches, or a plurality of nonconsecutive mismatches. The maximum number of the mismatches can be any number as long as two strands of nucleic acids to be hybridized can be maintained in a double-stranded state. Accordingly, the maximum number varies depending on the number of nucleotides to be paired through hybridization, but is preferably 5 bases, more preferably 3 bases, and further preferably 2 bases.

The above-mentioned primer that causes a mismatch depending on the presence or absence of a mutation can be designed suitably by any person skilled in the art through the comparison between a target nucleic acid sequence containing a mutation to be detected and a target nucleic acid sequence that does not contain the mutation. That is, the primer is designed so as to hybridize to a region containing a nucleotide that is different between the above-mentioned two target nucleic acid sequences. In that case, when the primer is designed so as to contain a sequence that is complementary to the target nucleic acid sequence containing the mutation, the absence of the mutation causes a mismatch. On the other hand, when the primer is designed so as to contain a sequence that is complementary to the target nucleic acid sequence that does not contain the mutation, the presence of the mutation causes a mismatch.

According to a preferred embodiment, a first primer included in the above-mentioned primer set is the first primer that is included in the primer set of the present invention described above. This first primer can be designed so that at least one mismatch occurs between the sequence (A) and the sequence (Ac'), depending on the presence or absence of the mutation. This first primer also can be designed so that at least one mismatch occurs between the sequence (Bc) and the sequence (B'), depending on the presence or absence of the mutation.

According to another preferred embodiment, a second primer included in the above-mentioned primer set is the second primer that is included in the primer set of the present invention described above. This second primer can be designed so that at least one mismatch occurs between the sequence (C) and the sequence (Cc'), depending on the presence or absence of the mutation.

According to another preferred embodiment, the primer set further includes the third primer that may be included in the primer set of the present invention described above. This third primer can be designed so that when the third primer hybridizes to the nucleic acid sequence contained in the nucleic acid sample or the complementary sequence thereto, at least one mismatch occurs between the third primer and the nucleic acid sequence or the complementary sequence thereto, depending on the presence or absence of the mutation.

Other conditions for the above-mentioned nucleic acid amplification reaction can be determined in the same manner as in the nucleic acid amplification method of the present invention. For instance, in the above-mentioned nucleic acid amplification reaction, it is preferable that the aforementioned polymerase having strand displacement ability be used. Furthermore, the aforementioned melting temperature adjusting agent, enzyme stabilizing agent, etc. may be used, if necessary.

As a result of performing the mutation detection method according to this embodiment, when an amplification product was obtained using the primer that allows a mismatch to be caused by the presence of a mutation, it can be judged that the mutation is absent in the nucleic acid sample, while it can be judged that the mutation is present when no amplification product was obtained. On the other hand, when an amplification product was obtained using the primer that allows a mismatch to be caused by the absence of a mutation, it can be judged that the mutation is present in the nucleic acid sample, while it can be judged that the mutation is absent when no amplification product was obtained.

In order to carry out the mutation detection method according to the second aspect of the present invention according to this embodiment, necessary reagents can be put together into a kit. Hence, the kit includes the substance having mismatch recognition ability and the primer set. Preferably, the kit further includes the above-mentioned polymerase having strand displacement ability. Moreover, the kit may include the above-mentioned melting temperature adjusting agent, enzyme stabilizing agent, reagents such as dNTP, a buffer solution, etc., a reaction vessel, an instruction manual, etc.

According to another embodiment, the mutation detection method according to the second aspect of the present invention includes the following processes:
(a) a process of preparing a nucleic acid sample;
(b) a process of preparing a primer set that allows a target nucleic acid sequence containing a site associated with a mutation to be amplified;
(c) a process of preparing a nucleic acid fragment that hybridizes to the target nucleic acid sequence and that is designed so that when the nucleic acid fragment hybridizes to a nucleic acid sequence contained in the nucleic acid sample or a complementary sequence thereto, at least one mismatch occurs between the nucleic acid fragment and the nucleic acid sequence or the complementary sequence thereto, depending on the presence or absence of the mutation; and
(d) a process of performing a nucleic acid amplification reaction in the presence of a substance having mismatch recognition ability and the nucleic acid fragment, using the primer set in which the nucleic acid sample serves as a template.

The at least one mismatch described above can be a mismatch of one base, a plurality of consecutive mismatches, or a plurality of nonconsecutive mismatches. The maximum number of the mismatches can be any number as long as two strands of nucleic acids to be hybridized can be maintained in a double-stranded state. Accordingly, the maximum number varies depending on the number of nucleotides to be paired through hybridization, but is preferably 5 bases, more preferably 3 bases, and further preferably 2 bases.

The above-mentioned nucleic acid fragment that causes a mismatch depending on the presence or absence of a mutation can be designed suitably by any person skilled in the art through the comparison between a target nucleic acid sequence containing a mutation to be detected and a target nucleic acid sequence that does not contain the mutation. That is, the nucleic acid fragment is designed so as to hybridize to a region containing a nucleotide that is different between the above-mentioned two target nucleic acid sequences. In that case, when the nucleic acid fragment is designed so as to contain a sequence that is complementary to the target nucleic acid sequence containing the mutation, the absence of the mutation causes a mismatch. On the other hand, when the nucleic acid fragment is designed so as to contain a sequence that is complementary to the target nucleic acid sequence that does not contain the mutation, the presence of the mutation causes a mismatch.

The nucleic acid fragment can be any nucleic acid fragment as long as it hybridizes to a target nucleic acid sequence at a temperature to be employed for the nucleic acid amplification reaction, for example, a temperature in the range of 20° C. to 80° C. The strand length of the nucleic acid fragment is not particularly limited but is preferably 5 to 40 nucleotides and more preferably 15 to 25 nucleotides. The nucleic acid fragment can contain modified bases (bases that do not exist in natural), if necessary. Furthermore, the nucleic acid fragment may contain a label or an active group such as an amino group at one or both of its ends.

The above-mentioned primer set that allows a target nucleic acid sequence to be amplified can be designed suitably according to the nucleic acid amplification method to be employed. Particularly, it is preferable that the primer set allow a target nucleic acid sequence to be amplified isothermally. In that case, the nucleic acid amplification reaction can be performed isothermally.

According to a preferred embodiment, a first primer included in the above-mentioned primer set is the first primer that is included in the primer set of the present invention described above. According to another preferred embodiment, a second primer included in the above-mentioned primer set is the second primer that is included in the primer set of the present invention described above. According to still another preferred embodiment, the primer set further includes the third primer that may be included in the primer set of the present invention described above.

Other conditions for the above-mentioned nucleic acid amplification reaction can be determined in the same manner as in the nucleic acid amplification method of the present invention. For instance, in the above-mentioned nucleic acid amplification reaction, it is preferable that the aforementioned polymerase having strand displacement ability be used. Furthermore, the aforementioned melting temperature adjusting agent, enzyme stabilizing agent, etc. may be used, if necessary.

As a result of performing the mutation detection method according to this embodiment, when an amplification product was obtained using the nucleic acid fragment that allows a mismatch to be caused by the presence of a mutation, it can be judged that the mutation is absent in the nucleic acid sample, while it can be judged that the mutation is present when no amplification product was obtained. On the other hand, when an amplification product was obtained using the nucleic acid fragment that allows a mismatch to be caused by the absence of a mutation, it can be judged that the mutation is present in the nucleic acid sample, while it can be judged that the mutation is absent when no amplification product was obtained.

In order to carry out the mutation detection method according to the second aspect of the present invention according to this embodiment, necessary reagents can be put together into a kit. Hence, the kit includes the substance having mismatch recognition ability, the primer set, and the nucleic acid fragment. Preferably, the kit further includes the above-mentioned polymerase having strand displacement ability. Moreover, the kit may include the above-mentioned melting temperature adjusting agent, enzyme stabilizing agent, reagents such as dNTP, a buffer solution, etc., a reaction vessel, an instruction manual, etc.

EXAMPLES

Hereinafter, the present invention is described further in detail using examples. However, the scope of the present invention is not limited to the examples.

Example 1

Amplification of Target Nucleic Acid Sequence Contained in Human STS DYS237 Gene In this example, Human Genomic DNA (manufactured by Clontech) was used as a template, and a target nucleic acid sequence in the human STS DYS237 gene contained therein was amplified. A primer pair having the sequences described below was used as primers. The positional relationship of each primer region to the template was set as shown in FIG. 4 (SEQ ID NO: 6). A forward primer F1 is designed so as to have the structure shown in FIG. 2 in which the sequence (22 mer: the underlined portion) that is located on its 3' end side anneals to the template, while the sequence (16 mer: the portion other than the underlined portion) that is located on the 5' end side is folded in that region. A reverse primer R1 is designed so that the sequence (20 mer: the underlined portion) that is located on its 3' end side anneals to the template, while after an extension reaction, the sequence (10 mer: the portion other than the underlined portion) that is located on the 5' end side hybridizes to the region starting from 16 bases downstream of residues located at the 3' end of the primer on the strand extended by the primer.

```
Primer Pair:
F1:
GGATATATATATATCCACTGAACAAATGCCACATAA (SEQ ID NO: 1)

AG;
and

R1:
GCAGCATCACCAACCCAAAAGCACTGAGTA.      (SEQ ID NO: 2)
```

A reaction solution (25 µL) having the following composition was prepared: Tris-HCl (20 mM, pH 8.8), KCl (10 mM), $(NH_4)_2SO_4$ (10 mM), $MgSO_4$ (8 mM), DMSO (3%), Triton X-100 (1%), dNTP (1.4 mM), 2000 nM of each primer of the above-mentioned primer pair, a template (100 ng), and 16U Bst DNA polymerase (NEW ENGLAND BioLabs). This was incubated at 60° C. for one hour. The template was allowed to react while being maintained in the double-stranded state. The same experiment was carried out with respect to a solution in which sterile water was added instead of the template.

Figure 5:
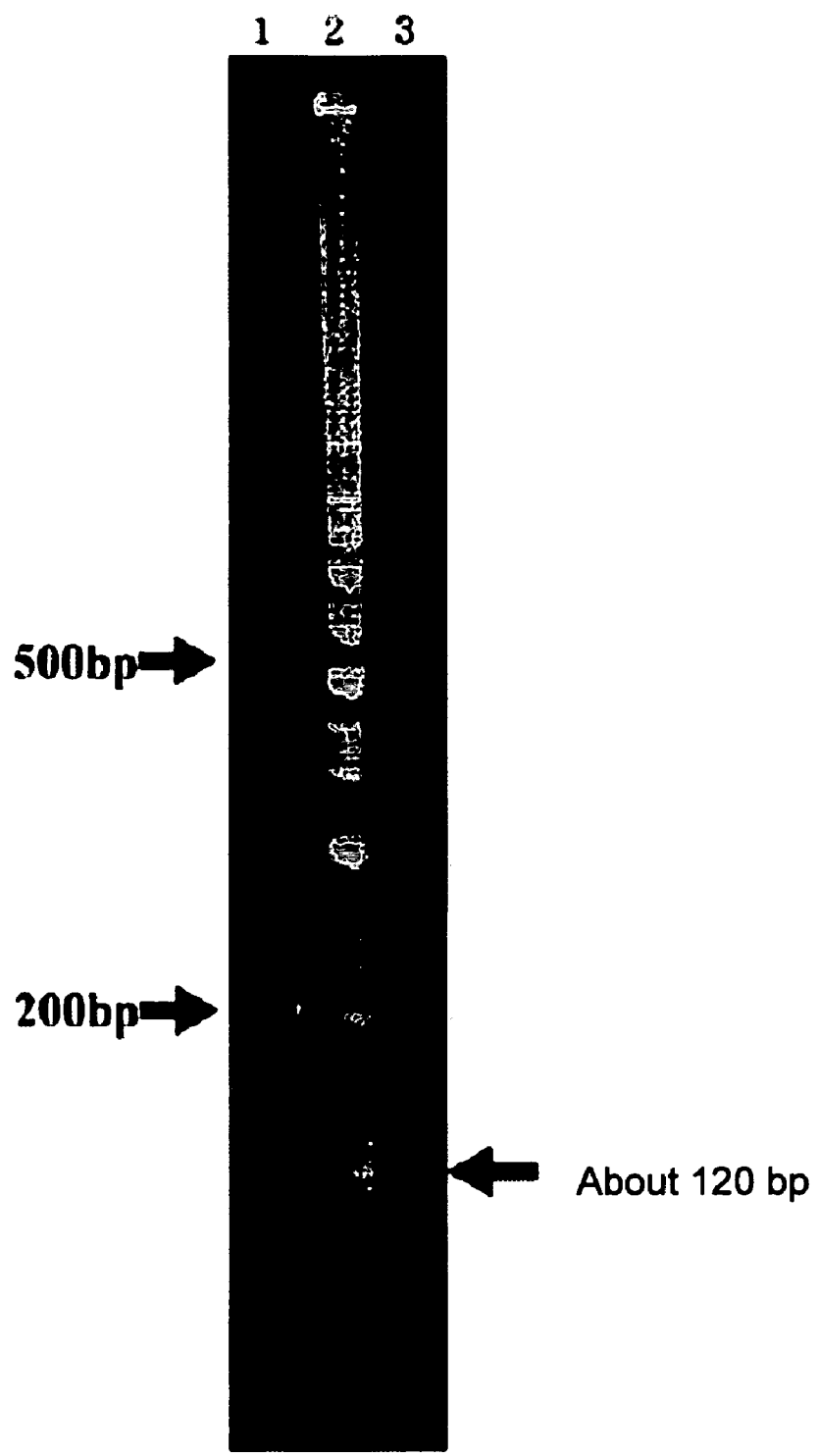
FIG. 5 is a diagram showing results of the amplification of the human STS DYS237 gene that was performed using a primer set including the first primer and the second primer.

With respect to each reaction solution 5 µl, electrophoresis was carried out at 100 V for 80 minutes using 3% NuSieve 3:1 Agarose (manufactured by BioWhittaker Molecular Applications (BMA) Inc.; purchased from TAKARA BIO INC.; "NuSieve" is a registered trademark of BMA Inc.). After the electrophoresis, the gel thus obtained was stained with ethidium bromide (EtBr) and thereby nucleic acids were detected. The results are shown in FIG. 5. The samples in the respective lanes shown in FIG. 5 are as follows: Lane 1: 20 bp DNA Ladder size marker; Lane 2: a reaction solution containing a template; and Lane 3: a reaction solution in which sterile water was added instead of the template.

In Lane 3 shown in FIG. 5, no bands were observed other than those of stained unreacted primers. In Lane 2, among the small size bands, the band located around 120 bp is expected as an amplification product of the target nucleic acid. Thus, an amplification product was observed in the reaction solution containing the template. In Lane 2, further, bands were observed above the amplification product. They are amplification products that contain the target nucleic acid sequence repeatedly, which are predicted in the amplification reaction according to the present invention. The amplification products obtained through the amplification reaction according to the present invention have complicated structures. As a result, such a ladder-like electrophoresis result was obtained.

Example 2

Cleavage by Restriction Enzyme

In order to prove that the amplification products obtained in Example 1 were derived from the target nucleic acid sequence, the amplification products were digested with a restriction enzyme. Specifically, 0.3 µL of the reaction solution obtained after the amplification reaction in Example 1 was digested (at 37° C. for three hours) with a restriction enzyme MboII.

Figure 6:
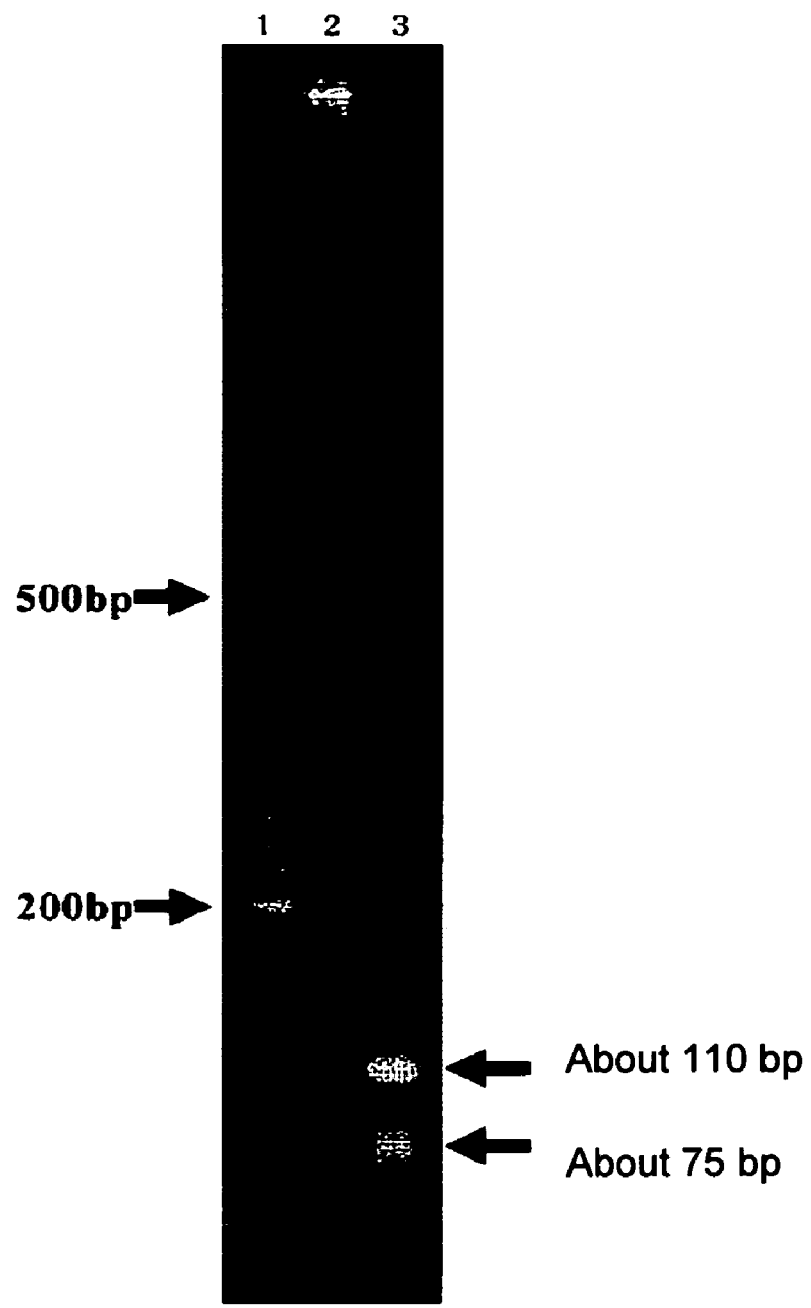
FIG. 6 is a diagram showing results obtained by treating an amplification product with a restriction endonuclease after the amplification of the human STS DYS237 gene that was performed using the primer set including the first primer and the second primer.

The digestion product was electrophoresed using 3% NuSieve 3:1 Agarose (manufactured by BioWhittaker Molecular Applications (BMA) Inc.; purchased from TAKARA BIO INC.; "NuSieve" is a registered trademark of BMA Inc.) The results are shown in FIG. 6. The samples in the respective lanes shown in FIG. 6 are as follows: Lane 1:20 bp DNA Ladder size marker; Lane 2: a product obtained through electrophoresis of 0.3-µL amplification product subjected to no further processing; and Lane 3: a product obtained through electrophoresis of the digestion product of 0.3-µL amplification product.

In FIG. 6, the size of each fragment digested with the restriction enzyme that is predicted from the nucleotide sequence is indicated on the right-hand side of the electropherogram. Since the bands of the undigested sample were changed into the bands with predicted sizes after the digestion, it was proved that the target nucleic acid sequence had been amplified.

Example 3

Enhancement of Amplification Reaction through Addition of Melting Temperature Adjusting Agent A melting temperature adjusting agent was added to an amplification reaction solution, and its effect on the amplification efficiency was examined. As in Example 1, Human DNA (manufactured by Clontech) was used as a template, and a target nucleic acid sequence contained in a human STS DYS237 gene was amplified. The composition of the amplification reaction solution was the same as that in Example 1 except that DMSO whose final concentration was 0%, 2%, 5%, or 10% was added as a melting temperature adjusting agent. The reaction conditions as well as the conditions for the electrophoresis carried out after the reaction were the same as those described in Example 1.

Figure 7:
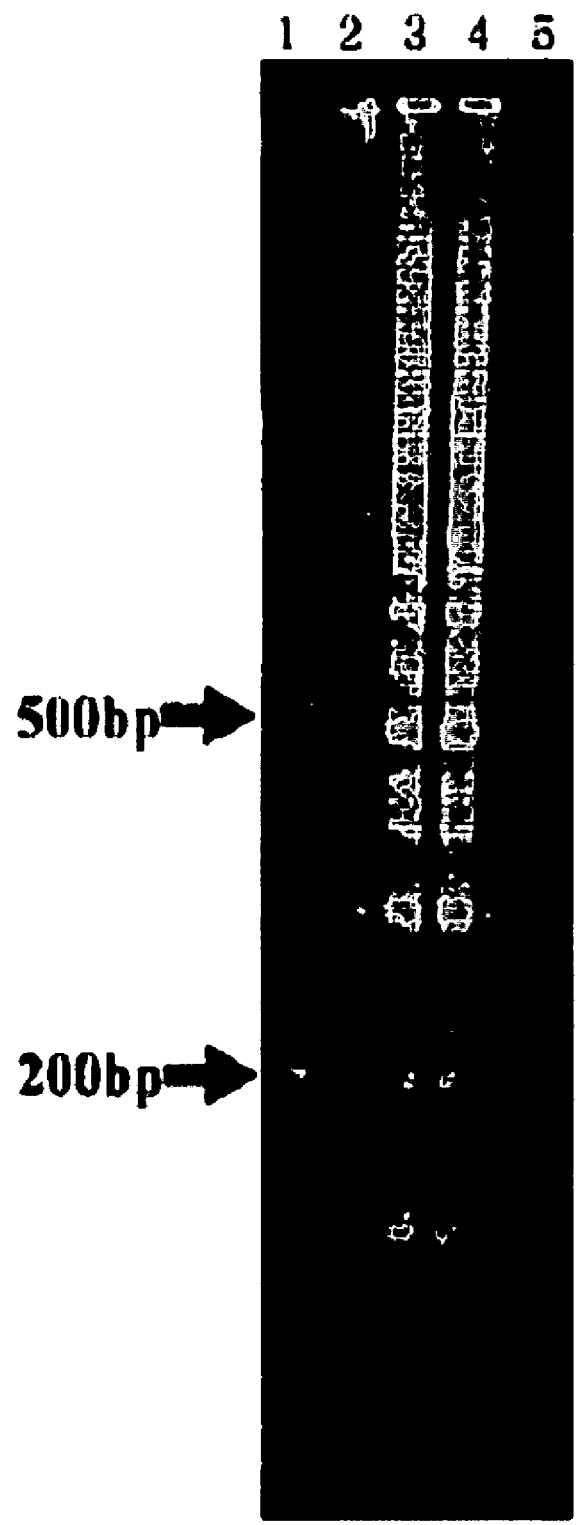
FIG. 7 is a diagram illustrating the influence of a melting temperature adjusting agent on the amplification of the human STS DYS237 gene that is performed using the primer set including the first primer and the second primer.

The results are shown in FIG. 7. The samples in the respective lanes shown in FIG. 7 are as follows: Lane 1: 20 bp DNA Ladder size marker; Lane 2: 0% DMSO (DMSO is not contained); Lane 3: 2% DMSO; Lane 4: 5% DMSO; and Lane 5: 10% DMSO.

As is clear from FIG. 7, in each case of 2% DMSO and 5% DMSO, a sufficient amount of amplification product was obtained. In the case of 0% DMSO, a small amount of amplification product was obtained. On the other hand, in the case of 10% DMSO, no amplification product was obtained. Conceivably, this is because the concentration of the melting temperature adjusting agent was too high and thereby the melting temperature Tm decreased excessively.

Example 4

Detection of Single Nucleotide Mutation

In this example, a single nucleotide mutation was detected using a primer set of the present invention. First, in order to prepare a model of single nucleotide mutation, a long-chain synthetic oligonucleotide that contained a single nucleotide mutation in a specific region of a human STS DYS237 gene and a long-chain synthetic oligonucleotide that contained no single nucleotide mutation were synthesized. These long-chain synthetic oligonucleotides each were amplified by the PCR method. As a result, amplification products of a wild-type DNA that contained no single nucleotide mutation and a mutated-type DNA that contained a single nucleotide mutation were obtained. Each of the amplification products was sequenced and the nucleotide residue located in the mutated portion was determined. Thereafter, they were used for the following experiment, as templates. FIG. 8 (SEQ ID NO: 7 and SEQ ID NO: 8) shows the nucleotide sequences of the amplification products. As is clear from FIG. 8, the residue indicated with the arrow that is a C residue in the wild-type DNA was replaced by a G residue in the mutated-type DNA.

The primers used herein were a primer pair for detecting a wild-type DNA and a primer pair for detecting a mutated-type DNA that had the sequences described below. In the primer pair for detecting a wild-type DNA, the primer F1 and the primer R1 that were used in Example 1 were employed as a forward primer and a reverse primer, respectively. In the primer pair for detecting a mutated-type DNA, the above-mentioned primer F1 was used as a forward primer while a newly designed primer R1G was used as a reverse primer. The primer R1G has the same nucleotide sequence as that of the primer R1 except for having a G residue at the fifth site from the 5' end. The positional relationship of each primer region to the template DNA was shown in FIG. 8.

```
Primer pair for detecting a wild-type DNA:
F1:
GGATATATATATATCCACTGAACAAATGCCACATAA (SEQ ID NO: 1)

AG;
and

R1:
GCAGCATCACCAACCCAAAAGCACTGAGTA.        (SEQ ID NO: 2)

Primer pair for detecting a mutated-type DNA:
F1:
GGATATATATATATCCACTGAACAAATGCCACATAA (SEQ ID NO: 1)

AG;
and

R1G:
GCAGGATCACCAACCCAAAAGCACTGAGTA.       (SEQ ID NO: 3)
```

The above-mentioned wild-type DNA or mutated-type DNA was used as a template. With respect to each case, the nucleic acid amplification reaction was conducted using the primer pair for detecting a wild-type DNA or the primer pair for detecting a mutated-type DNA. Specifically, a reaction solution (25 µL) having the following composition was prepared: Tris-HCl (20 mM, pH 8.8), KCl (10 mM), $(NH_4)_2SO_4$ (10 mM), $MgSO_4$ (8 mM), DMSO (3%), Triton X-100 (1%), dNTP (1.4 mM), 2000 nM of each primer of the above-mentioned primer pairs, a template ($10^{-19}$ mol/tube (about 60000 molecules)), and 16U Bst DNA polymerase (NEW ENGLAND BioLabs). This was incubated at 60° C. for one hour. The template was allowed to react while being maintained in the double-stranded state.

Figure 9:
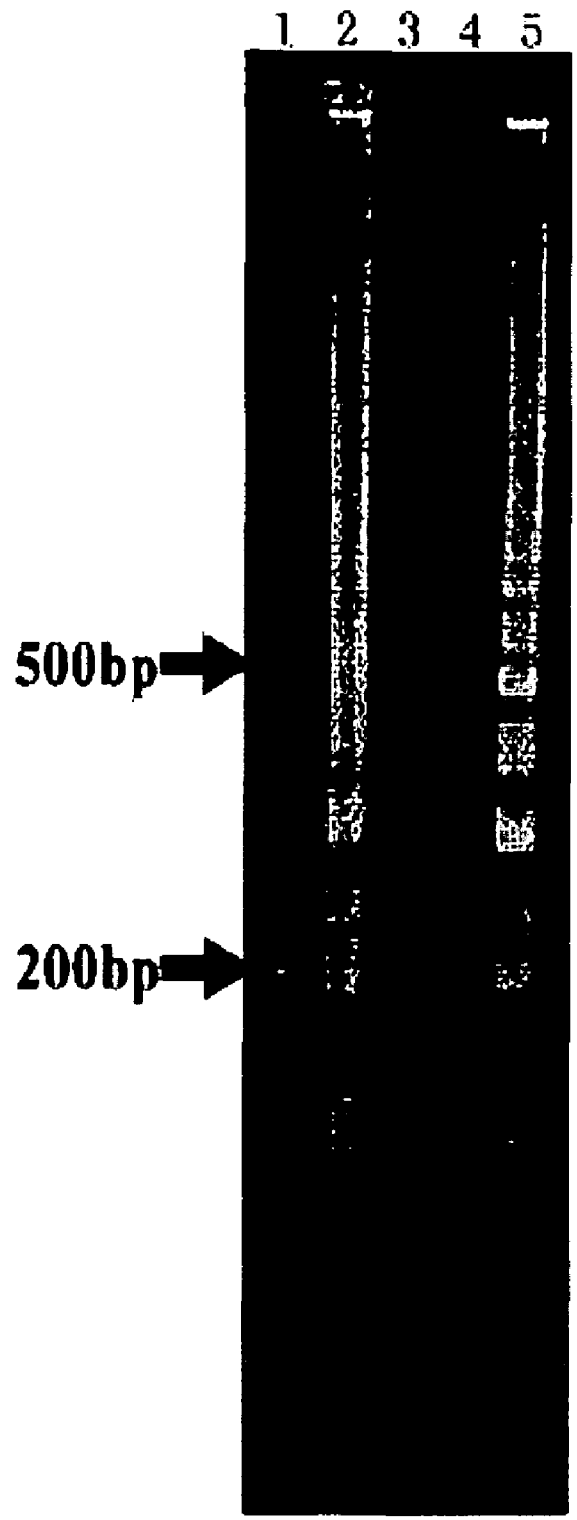
FIG. 9 is a diagram showing results of the detection of a single nucleotide mutation that was performed using the primer set including first primers and second primers, with respect to a specific region of the human STS DYS237 gene.

With respect to 5 µl of each reaction solution, electrophoresis was carried out at 100 V for 80 minutes using 3% NuSieve 3:1 Agarose (manufactured by BioWhittaker Molecular Applications (BMA) Inc.; purchased from TAKARA BIO INC.; "NuSieve" is a registered trademark of BMA Inc.). After the electrophoresis, the gel thus obtained was stained with ethidium bromide (EtBr) and thereby nucleic acids were detected. The results are shown in FIG. 9. The samples in the respective lanes shown in FIG. 9 are as follows: Lane 1:20 bp DNA Ladder size marker; Lane 2: a reaction solution obtained using the wild-type DNA as a template and the primer pair for detecting a wild-type DNA; Lane 3: a reaction solution obtained using the mutated-type DNA as a template and the primer pair for detecting a wild-type DNA; Lane 4: a reaction solution obtained using the wild-type DNA as a template and the primer pair for detecting a mutated-type DNA; and Lane 5: a reaction solution obtained using the mutated-type DNA as a template and the primer pair for detecting a mutated-type DNA.

As is apparent from FIG. 9, in Lanes 2 and 5, amplification products were obtained. In these lanes, among the small size bands, the bands located around 120 bp are expected as amplification products of the target nucleic acid. On the other hand, in Lanes 3 and 4, no amplification product was obtained. Hence, it was proved that the primer pair for detecting a wild-type DNA detected the wild-type DNA alone while the primer pair for detecting a mutated-type DNA detected the mutated-type DNA alone. These results indicated that the use of the amplification reaction according to the present invention allowed a single nucleotide mutation to be detected effectively.

Example 5

Acceleration of Amplification Rate through Addition of Third Primer

A nucleic acid amplification reaction was conducted using third primers in addition to the primer pair used in Example 1. The third primers used herein were two primers having the sequences described below. These third primers were designed so as to anneal to different locations from those to which the above-mentioned primer pair annealed, on the target nucleic acid sequence to be amplified using the above-mentioned primer pair. The positional relationship of each primer region to the template was set as shown in FIG. 10 (SEQ ID NO: 6).

```
Third Primers:
Primer 3F:      TAAGAACTCGCTTTATAC;  (SEQ ID NO: 4)
and

Primer 3R:      TCTTCAACAGTCATTACC.  (SEQ ID NO: 5)
```

As in Example 1, Human DNA (manufactured by Clontech) was used as a template, and a target nucleic acid sequence contained in a human STS DYS237 gene was amplified. The composition of the amplification reaction solution was the same as that employed in Example 1 except for containing one or both of the primer 3F (800 nM) and the primer 3R (800 nM) as the third primer. This reaction solution was incubated at 60° C. for 30 minutes or 60 minutes.

Figure 11:
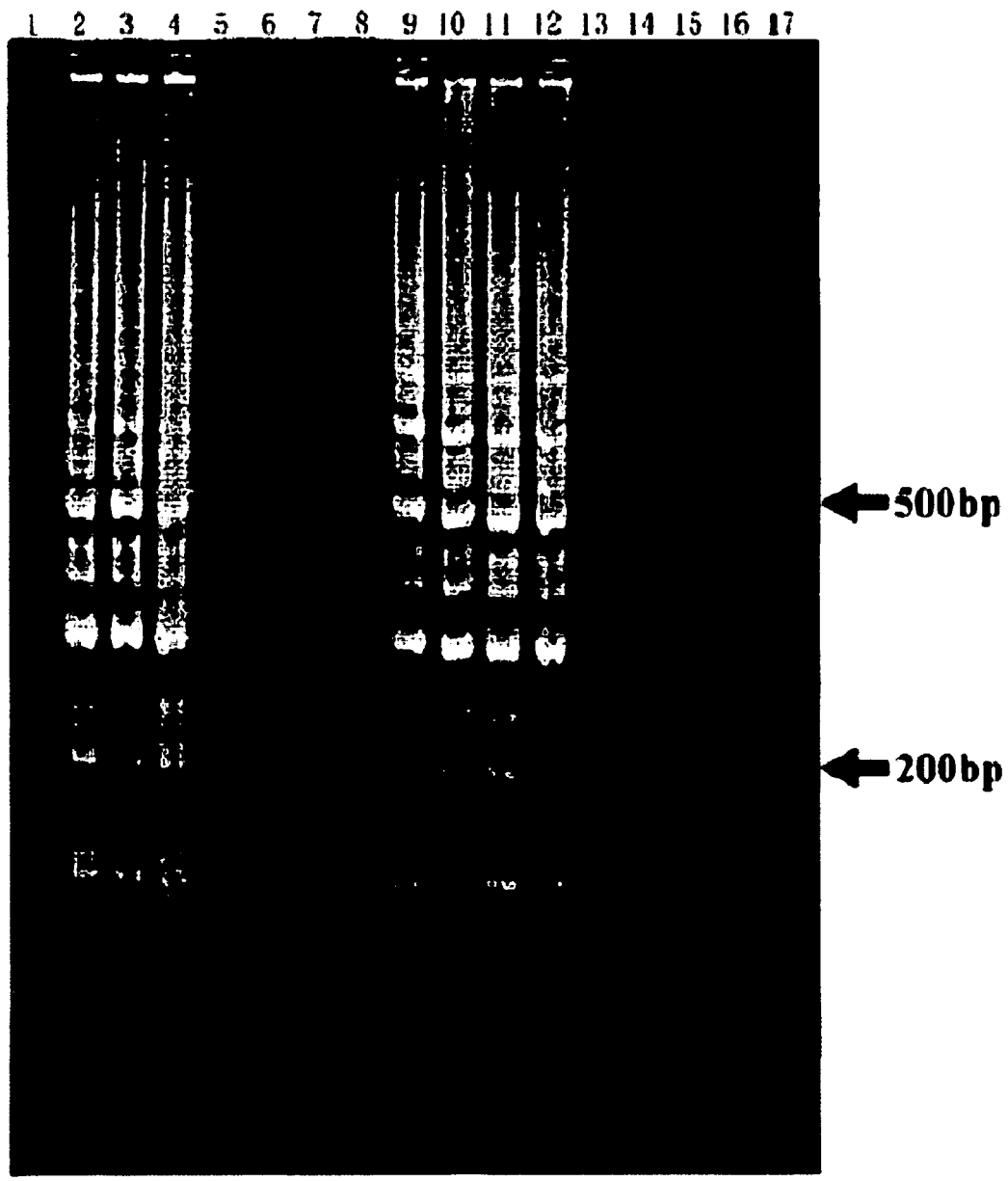
FIG. 11 is a diagram showing results of the amplification of the human STS DYS237 gene that was performed using a primer set including the first primer, the second primer, and the third primers.

With respect to each reaction solution 5 µl, electrophoresis was carried out at 100 V for 80 minutes using 3% NuSieve 3:1 Agarose (manufactured by BioWhittaker Molecular Applications (BMA) Inc.; purchased from TAKARA BIO INC.; "NuSieve" is a registered trademark of BMA Inc.). After the electrophoresis, the gel thus obtained was stained with ethidium bromide (EtBr) and thereby nucleic acids were detected. The results are shown in FIG. 11. The samples in the respective lanes shown in FIG. 11 are indicated in Table 1 below.

TABLE 1

Samples in Respective Lanes on Electropherogram shown in FIG. 11

| Lane | Third Primer | Template DNA | Amplification Reaction Time (min) |
|---|---|---|---|
| 1 | None | Yes | 30 |
| 2 | 3F | Yes | 30 |
| 3 | 3R | Yes | 30 |
| 4 | 3F + 3R | Yes | 30 |
| 5 | None | No | 30 |
| 6 | 3F | No | 30 |
| 7 | 3R | No | 30 |

TABLE 1-continued

Samples in Respective Lanes on Electropherogram shown in FIG. 11

| Lane | Third Primer | Template DNA | Amplification Reaction Time (min) |
|---|---|---|---|
| 8 | 3F + 3R | No | 30 |
| 9 | None | Yes | 60 |
| 10 | 3F | Yes | 60 |
| 11 | 3R | Yes | 60 |
| 12 | 3F + 3R | Yes | 60 |
| 13 | None | No | 60 |
| 14 | 3F | No | 60 |
| 15 | 3R | No | 60 |
| 16 | 3F + 3R | No | 60 |
| 17 | 20 bp DNA Ladder size marker | | |

In the electropherogram shown in FIG. 11, among the small size bands, the bands located around 120 bp are expected as amplification products of the target nucleic acid. As is clear from FIG. 11, in each of the samples containing one or two third primers added thereto, a sufficient amount of amplification product was obtained through the reaction that was performed for 30 minutes or 60 minutes (Lanes 2 to 4 and Lanes 10 to 12). On the other hand, in the samples containing no third primer added thereto, no amplification product was obtained through the reaction that was performed for 30 minutes (Lane 1) but an amplification product was obtained through the reaction that was performed for 60 minutes (Lane 9). In the samples that contained no template added thereto, no amplification product was obtained (Lanes 5 to 8 and Lanes 13 to 16). These results indicated that the addition of the third primer allowed the amplification efficiency to be improved in the amplification reaction according to the present invention.

Example 6

Check for Template Concentration-Dependent Amplification

A reaction solution was prepared in the same manner as in Example 1 except for containing 100 ng, 10 ng, 1 ng, or 0 ng of Human Genomic DNA (manufactured by Clontech) as a template and 800 nM of the primer 3F (SEQ ID NO: 4) as a third primer. This reaction solution was incubated at 60° C. for 20 minutes, 40 minutes, or 60 minutes.

Figure 12:
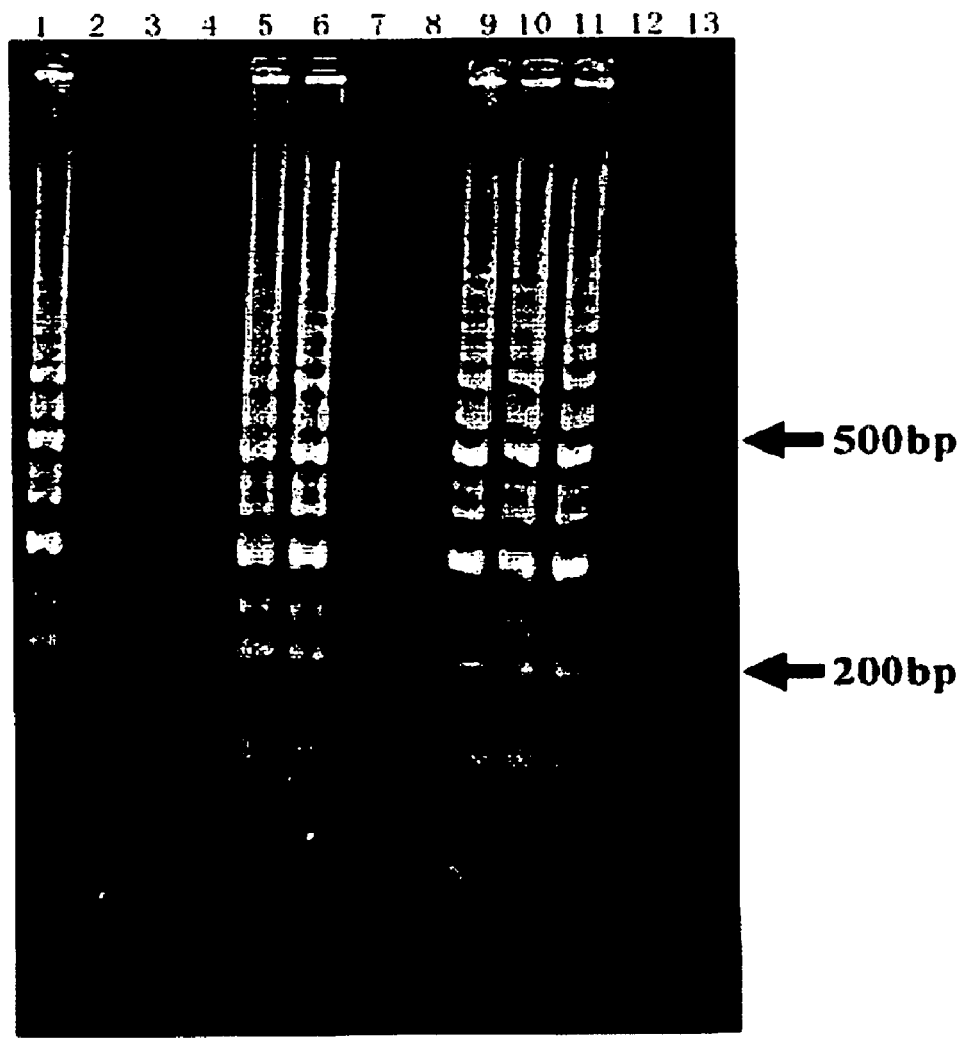
FIG. 12 is a diagram illustrating the influence of the template concentration on the amplification of the human STS DYS237 gene that was performed using a primer set including the first primer, the second primer, and a third primer.

With respect to each reaction solution 5 µl, electrophoresis was carried out at 100 V for 80 minutes using 3% NuSieve 3:1 Agarose (manufactured by BioWhittaker Molecular Applications (BMA) Inc.; purchased from TAKARA BIO INC.; "NuSieve" is a registered trademark of BMA Inc.). After the electrophoresis, the gel thus obtained was stained with ethidium bromide (EtBr) and thereby nucleic acids were detected. The results are shown in FIG. 12. The samples in the respective lanes shown in FIG. 12 are indicated in Table 2 below.

TABLE 2

Samples in Respective Lanes on Electropherogram shown in FIG. 12

| Lane | Template (ng) | Amplification Reaction Time (min) |
|---|---|---|
| 1 | 100 | 20 |
| 2 | 10 | 20 |
| 3 | 1 | 20 |

TABLE 2-continued

Samples in Respective Lanes on Electropherogram shown in FIG. 12

| Lane | Template (ng) | Amplification Reaction Time (min) |
|---|---|---|
| 4 | 0 | 20 |
| 5 | 100 | 40 |
| 6 | 10 | 40 |
| 7 | 1 | 40 |
| 8 | 0 | 40 |
| 9 | 100 | 60 |
| 10 | 10 | 60 |
| 11 | 1 | 60 |
| 12 | 0 | 60 |
| 13 | 20 bp DNA Ladder size marker | |

In the electropherogram shown in FIG. 12, among the small size bands, the bands located around 120 bp are expected as amplification products of the target nucleic acid. As is clear from FIG. 12, when 100 ng of template was added, an amplification product was obtained through any one of reactions performed for 20 minutes or longer (Lanes 1, 5, and 9). When 10 ng of template was added, an amplification product was obtained through each of the reactions performed for 40 minutes or longer (Lanes 6 and 10). When 1 ng of template was added, an amplification product was obtained through the reaction that was performed for at least 60 minutes (Lane 11). When the template was not added, no amplification product was obtained with respect to all the reaction times (Lanes 4, 8, and 12). From these results, it was proved that an increase in reaction time allowed an amplification product to be obtained even when the concentration of the template was low.

Example 7

Effect of MutS in Detection of Single Nucleotide Mutation in ALDH2 Gene

In this example, a single nucleotide mutation that existed in exon 12 of an aldehyde dehydrogenase-2 gene (ALDH2 gene) was detected using Human Genomic DNA (manufactured by Clontech) as a template. The above-mentioned DNA to be used as a template contained a wild-type ALDH2 gene.

Figure 13:
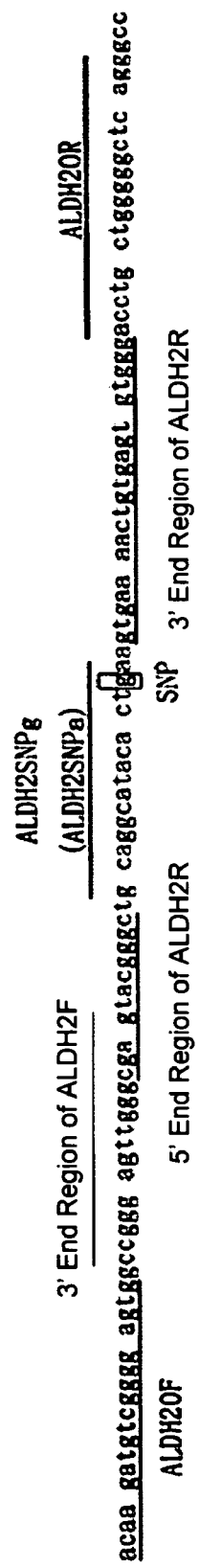
FIG. 13 shows the locations, on a human ALDH2 gene, of respective primers included in a primer set used for detecting a mutation in the above-mentioned gene.

A primer set having the sequences described below was used as primers. The positional relationship of each primer region to the template was set as shown in FIG. 13 (SEQ ID NO: 9). The forward primer ALDH2F is designed so as to have the structure shown in FIG. 2 in which the sequence (16 mer: the underlined portion) that is located on its 3' end side anneals to the template, while the sequence (16 mer: the portion other than the underlined portion) that is located on the 5' end side is folded in that region. The reverse primer ALDH2R is designed so that the sequence (20 mer: the underlined portion) that is located on the 3' end side anneals to the template, while after the extension reaction, the sequence (11 mer) that is located on the 5' end side hybridizes to the region starting from 18 bases downstream of residues located at the 3' end of the primer on the strand extended by the primer. The primers ALDH2OF and ALDH2OR are designed so as to anneal on the outer side (5' side) with respect to the ALDH2F and ALDH2R on the template, respectively. In addition, ALDH2SNPg and ALDH2SNPa each are a primer containing a nucleotide residue (the underlined portion) associated with a mutation. ALDH2SNPg contains a wild-type sequence while ALDH2SNPa contains a mutated-type sequence.

Sequences of Primers Used:

ALDH2F:
TTTATATATATATAAACCGGGAGTTGGGCGAG;    (SEQ ID NO: 10)

ALDH2R:
CGAGTACGGGCCCACACTCACAGTTTTCAC;     (SEQ ID NO: 11)

ALDH2OF:
ACAAGATGTCGGGGAGTG;                  (SEQ ID NO: 12)

ALDH2OR:
CCTGAGCCCCCAGCAGGT;                  (SEQ ID NO: 13)

ALDH2SNPg:
GCAGGCATACACTGA;                     (SEQ ID NO: 14)
and

ALDH2SNPa:
GCAGGCATACACTAA.                     (SEQ ID NO: 15)

A reaction solution (25 µL) having the following composition was prepared: Tris-HCl (20 mM, pH 8.8), KCl (10 mM), $(NH_4)_2SO_4$ (10 mM), $MgSO_4$ (6 mM), DMSO (6%), Triton X-100 (1%), dNTP (0.4 mM), 8U Bst DNA polymerase (NEW ENGLAND BioLabs), SYBR GREEN I (Molecular Probes, Inc.) (with a concentration that provided 100,000-fold dilution finally), a template (40 ng), 3200 nM of each of ALDH2F and ALDH2R, 400 nM of each of ALDH2OF and ALDH2OR, one of ALDH2SNPg (a wild-type primer) and ALDH2SNPa (a mutated-type primer) (1600 nM), and MutS (0.8 µg). This was incubated at 60° C. for 180 minutes. The template was allowed to react while being maintained in the double-stranded state. The same experiment was carried out with respect to a reaction solution containing no MutS. The production of amplification products was monitored using a real-time fluorescence detection system Mx3000P (manufactured by STRATAGENE).

Figure 14:
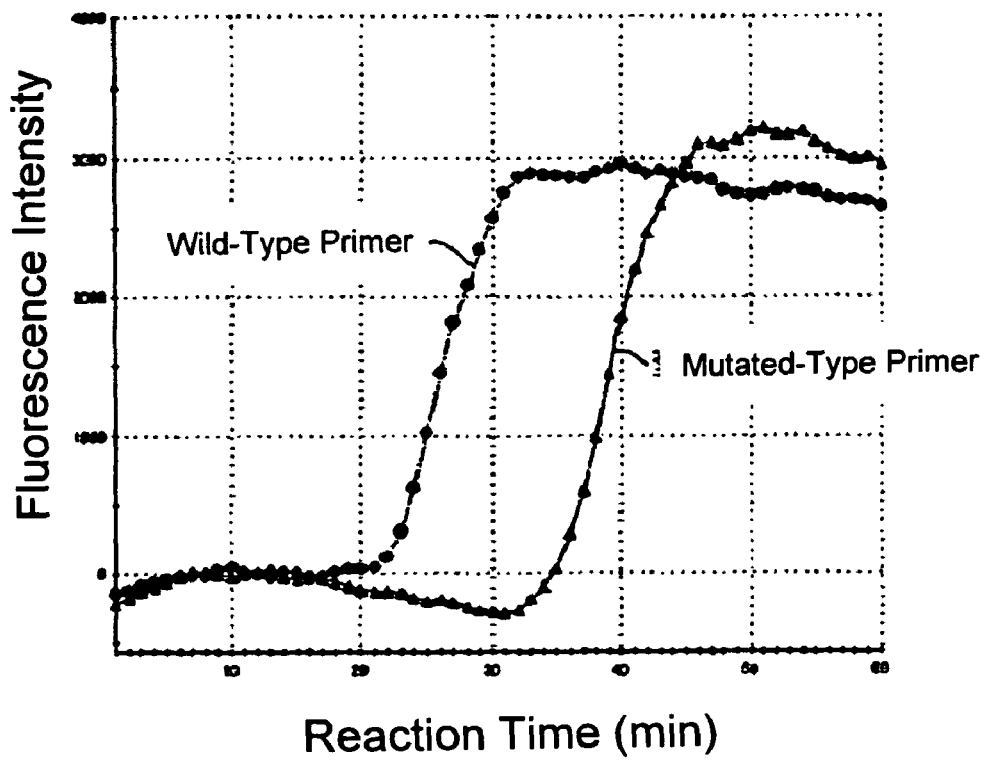
FIG. 14 shows graphs that indicate the effect of MutS on the detection of a single nucleotide mutation in the human ALDH2 gene that was carried out by utilizing the isothermal nucleic acid amplification reaction.
Figure 14:
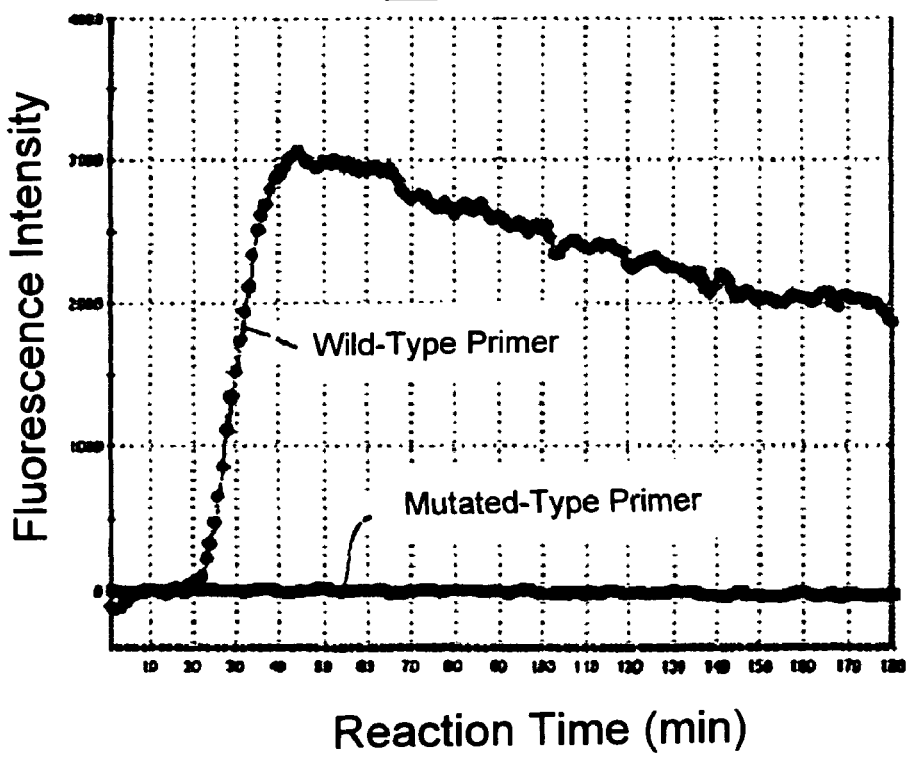

The results of the experiment are shown in FIG. 14. In this experiment, since the human genomic DNA containing no mutation was used as a template, an amplification product should be obtained when the above-mentioned wild-type primer was used, while no amplification product should be obtained when the mutated-type primer was used. According to FIG. 14, when the wild-type primer was used, the production of an amplification product was observed after about 25 minutes elapsed, irrespective of the presence of MutS. On the other hand, when the mutated-type primer was used, the production of an amplification product was observed in the absence of MutS after about 35 minutes elapsed, while the production of an amplification product was not observed in the presence of MutS even when the reaction was conducted for three hours. Thus, it was proved that the use of MutS made the correct SNP typing possible.

Example 8

Effect of MutS in Detection of Single Nucleotide Mutation in Human CYP2C19*3 Gene In this example, a single nucleotide mutation that existed in exon 4 of a CYP2C19*3 gene of drug-metabolizing enzyme-cytochrome P450 family was detected using Human Genomic DNA (manufactured by Clontech) as a template. In this example, the LAMP method was employed as the nucleic acid amplification method. The above-mentioned DNA to be used as a template contained a wild-type CYP2C19*3 gene.

Figure 15:
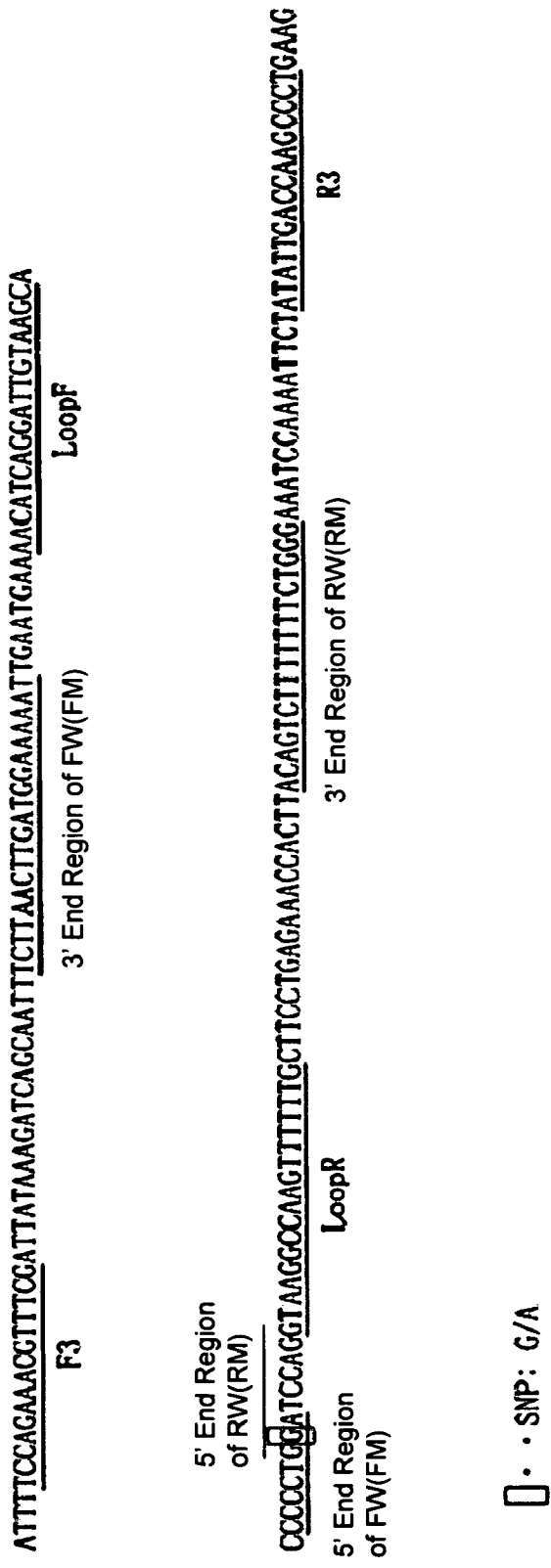
FIG. 15 shows the locations, on a human CYP2C19*3 gene, of respective primers included in a primer set used for detecting a mutation in the above-mentioned gene.

A primer set for the LAMP method having the sequences described below was used as primers. The positional relationship of each primer region to the template was set as shown in FIG. 15 (SEQ ID NO: 16). The forward primers FW and FM that are included in the respective inner primers each are designed so that the sequence (20 mer: the underlined portion) that is located on the 3' end side anneals to the template, while after the extension reaction, the sequence (8 mer) that is located on the 5' end side hybridizes to the region starting from 29 bases downstream of residues located at the 3' end of the primer on the strand extended by the primer. On the other hand, the reverse primers RW and RM that are included in the respective inner primers each are designed so that the sequence (18 mer: the underlined portion) that is located on the 3' end side anneals to the template, while after the extension reaction, the sequence (9 mer) that is located on the 5' end side hybridizes to the region starting from 36 bases downstream of residues located at the 3' end of the primer on the strand extended by the primer. The nucleotide residue located at the second site from the 5' end of each of the inner primers corresponds to the nucleotide residue associated with a mutation.

```
Wild-Type Inner Primer:
FW:
TCCAGGGGTCTTAACTTGATGGAAAAAT;      (SEQ ID NO: 17)
and

RW:
GGATCCAGGCCCAGAAAAAAAGACTGT,      (SEQ ID NO: 18)

Mutated-Type Inner Primer:
FM:
TTCAGGGGTCTTAACTTGATGGAAAAAT;     (SEQ ID NO: 19)
and

RM:
GAATCCAGGCCCAGAAAAAAAGACTGT,      (SEQ ID NO: 20)

Outer Primer:
F3:
TCCAGAAACGTTTCG;                   (SEQ ID NO: 21)
and

R3:
AGGGCTTGGTCAATAT,                  (SEQ ID NO: 22)
and

Loop Primer:
LoopF:
GCTTACAATCCTGATGTT;                (SEQ ID NO: 23)
and

LoopR:
GTAAGGCCAAGTTTTTTG.                (SEQ ID NO: 24)
```

A reaction solution (25 μL) having the following composition was prepared as a reaction solution containing a wild-type inner primer: Tris-HCl (20 mM, pH 8.8), KCl (10 mM), $(NH_4)_2SO_4$ (10 mM), $MgSO_4$ (4 mM), betaine (1 M), Tween20 (0.1%), dNTP (0.5 mM), 8U Bst DNA polymerase (NEW ENGLAND BioLabs), SYBR GREEN I (Molecular Probes, Inc.) (with a concentration that provided 100,000-fold dilution finally), a template (40 ng), 400 nM of each of F3 and R3, 800 nM of each of LoopF and LoopR, 1600 nM of each of FW and RW, and MutS (0.8 μg).

Furthermore, a reaction solution (25 μL) having the following composition was prepared as a reaction solution containing a mutated-type inner primer: Tris-HCl (20 mM, pH 8.8), KCl (10 mM), $(NH_4)_2SO_4$ (10 mM), $MgSO_4$ (4 mM), betaine (0.8 M), Tween20 (0.1%), dNTP (0.5 mM), 8U Bst DNA polymerase (NEW ENGLAND BioLabs), SYBR GREEN I (Molecular Probes, Inc.) (with a concentration that provided 100,000-fold dilution finally), a template (40 ng), 400 nM of each of F3 and R3, 800 nM of each of LoopF and LoopR, 1600 nM of each of FM and RM, and MutS (0.8 μg).

Each of the above-mentioned reaction solutions was incubated at 60° C. for 180 minutes. The template was allowed to react while being maintained in the double-stranded state. The same experiment was carried out with respect to a reaction solution containing no MutS. The production of amplification products was monitored using a real-time fluorescence detection system Mx3000P (manufactured by STRATAGENE).

Figure 16:
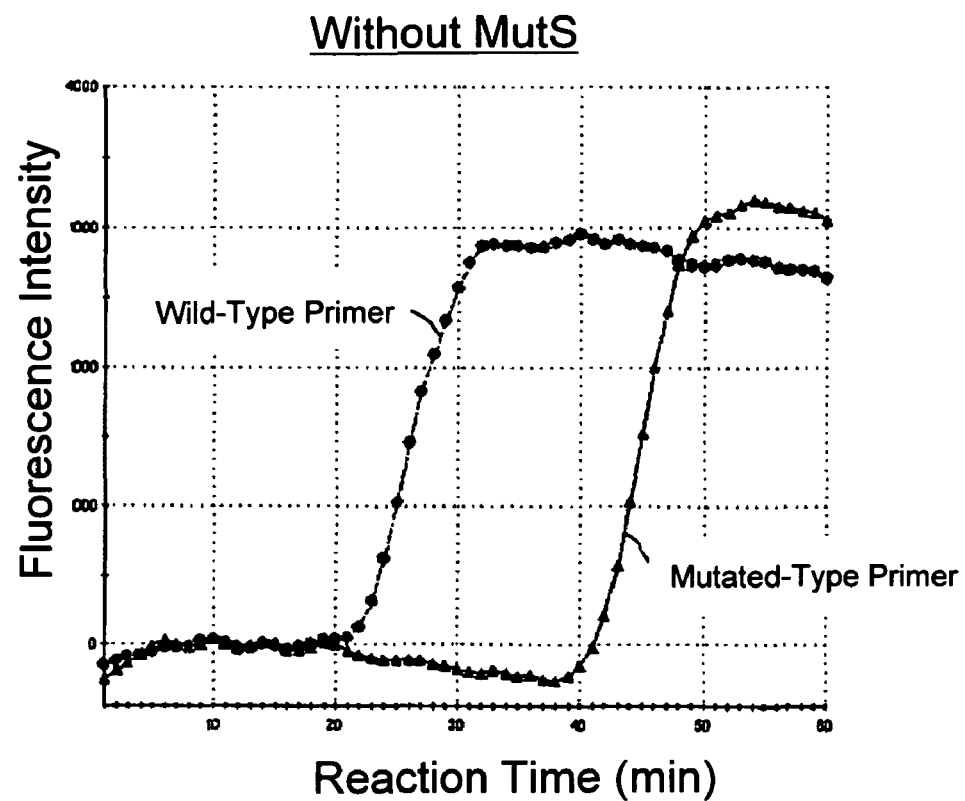
FIG. 16 shows graphs that indicate the effect of MutS on the detection of a single nucleotide mutation in the human CYP2C19*3 gene that was carried out by utilizing the isothermal nucleic acid amplification reaction.
Figure 16:
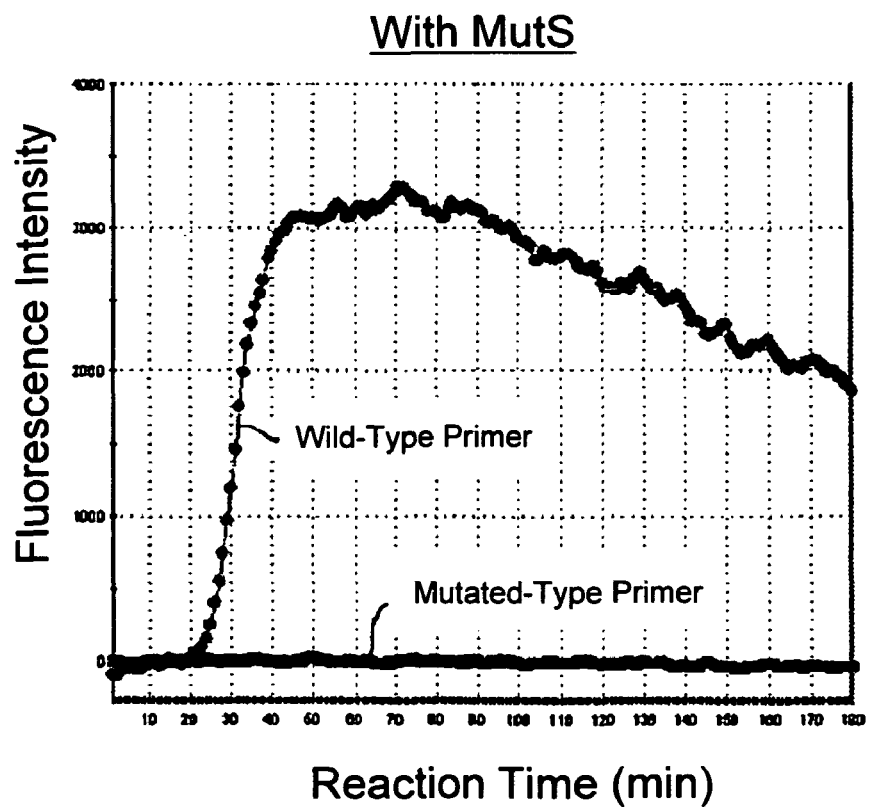

The results of the experiment are shown in FIG. 16. In this experiment, since the human genomic DNA containing no mutation was used as a template, an amplification product should be obtained when the above-mentioned wild-type inner primer was used, while no amplification product should be obtained when the mutated-type inner primer was used. According to FIG. 16, when the wild-type inner primer was used, the production of an amplification product was observed after about 25 minutes elapsed, irrespective of the presence of MutS. On the other hand, when the mutated-type inner primer was used, the production of an amplification product was observed in the absence of MutS after about 40 minutes elapsed, while the production of an amplification product was not observed in the presence of MutS even when the reaction was conducted for three hours. Thus, it was proved that the use of MutS made the correct SNP typing possible.

---

The invention claimed is:

1. A primer set comprising at least two primers that allows a target nucleic acid sequence to be amplified, wherein a first primer included in the primer set contains, in its 3' end portion, a sequence (Ac') that hybridizes to a sequence (A) located in the 3' end portion of the target nucleic acid sequence, and also contains, on the 5' side of the sequence (Ac'), a sequence (B') that hybridizes to a complementary sequence (Bc) to a sequence (B) that is present on the 5' side with respect to the sequence (A) in the target nucleic acid sequence, and a second primer included in the primer set contains, in its 3' end portion, a sequence (Cc') that hybridizes to a sequence (C) located in the 3' end portion of a complementary sequence to the target nucleic acid sequence, and also contains, on the 5' side of the sequence (Cc'), a folded sequence (D-Dc') that contains, on the same strand, two nucleic acid sequences that hybridize to each other.

2. The primer set according to claim 1, further comprising a third primer that hybridizes to the target nucleic acid sequence or the complementary sequence thereto, wherein the third primer does not compete with other primers for hybridization to the target nucleic acid sequence or the complementary sequence thereto.

3. The primer set according to claim 1, wherein in the first primer, when no intervening sequence is present between the sequence (Ac') and the sequence (B'), a ratio (X−Y)/X is in a range of −1.00 to 1.00, where X denotes the number of bases contained in the sequence (Ac') while Y indicates the number of bases contained in a region flanked by the sequence (A) and the sequence (B) in the target nucleic acid sequence, and when an intervening sequence is present between the sequence (Ac') and the sequence (B') in the primer, a ratio {X−(Y−Y')}/X is in a range of −1.00 to 1.00, where X and Y denote the same as described above, and Y' indicates the number of bases contained in the intervening sequence.

4. The primer set according to claim 1, wherein in the second primer, the folded sequence (D-Dc') has a length of 2 to 1000 nucleotides.

5. The primer set according to claim 1, wherein at least one primer included in the primer set has a solid-phase support or a site that can bind to a solid-phase support.

6. The primer set according to claim 5, wherein the solid-phase support is one selected from the group consisting of a water-insoluble organic polymer support, a water-insoluble inorganic polymer support, a synthetic polymer support, a phase transition support, a metal colloid, and a magnetic particle.

7. The primer set according to claim 5, wherein the site that can bind to a solid-phase support is selected from the group consisting of biotin, avidin, streptoavidin, an antigen, an antibody, a ligand, a receptor, a nucleic acid, and a protein.

* * * * *

SEQUENCE LISTING

```
<160> NUMBER OF SEQ ID NOS: 24

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence:Primer

<400> SEQUENCE: 1
ggatatatat atatccactg aacaaatgcc acataaag                              38

<210> SEQ ID NO 2
<211> LENGTH: 30
<212> TYPE: DNA
```

```
<213> ORGANISM: Artificial Sequence
<220> FEATURE:
<223> OTHER INFORMATION: Description of Artificial Sequence:Primer

<400> SEQUENCE: 2
gcagcatcac caacccaaaa gcactgagta                                        30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 3
gcaggatcac caacccaaaa gcactgagta                                        30

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 4
taagaactcg ctttatac                                                     18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 5
tcttcaacag tcattacc                                                     18

<210> SEQ ID NO 6
<211> LENGTH: 156
<212> TYPE: DNA
<213> ORGANISM: Homo sapiens

<400> SEQUENCE: 6
aagcttttaa agcatcctca tttatgtcc aacatcagag acttaatact gaacaaatgc        60
cacataaagg taatgactgt tgaagaagat ttaacttaac atcttgcagc atcactaaga      120
actcgcttta tactcagtgc ttttgggttg ggtttg                                156

<210> SEQ ID NO 7
<211> LENGTH: 108
<212> TYPE: DNA
<213> ORGANISM: Homo sapiens

<400> SEQUENCE: 7
aatactgaac aaatgccaca taaggtaat gactgttgaa gaagatttaa cttaacatct        60
tgcagcatca ctaagaactc gctttatact cagtgctttt ggttggg                   108

<210> SEQ ID NO 8
<211> LENGTH: 108
<212> TYPE: DNA
<213> ORGANISM: Homo sapiens

<400> SEQUENCE: 8
aatactgaac aaatgccaca taaggtaat gactgttgaa gaagatttaa cttaacatct        60
```

```
tgcaggatca ctaagaactc gctttatact cagtgctttt gggttggg            108

<210> SEQ ID NO 9
<211> LENGTH: 100
<212> TYPE: DNA
<213> ORGANISM: Homo sapiens

<400> SEQUENCE: 9
acaagatgtc ggggagtggc cgggagttgg gcgagtacgg gctgcaggca tacactgaag   60
tgaaaactgt gagtgtggga cctgctgggg gctcagggcc                       100

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 10
tttatatata tataaaccgg gagttgggcg ag                                32

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 11
cgagtacggg cccacactca cagttttcac                                   30

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 12
acaagatgtc ggggagtg                                                18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 13
cctgagcccc cagcaggt                                                18

<210> SEQ ID NO 14
<211> LENGTH: 15
<212> TYPE: DNA
<213> ORGANISM: Artificial Sequence
<220> FEATURE:
<223> OTHER INFORMATION: Description of Artificial
      Sequence:Oligonucleotide

<400> SEQUENCE: 14
gcaggcatac actga                                                   15

<210> SEQ ID NO 15
<211> LENGTH: 15
<212> TYPE: DNA
<213> ORGANISM: Artificial Sequence
```

-continued

```
<220> FEATURE:
<223> OTHER INFORMATION: Description of Artificial
      Sequence:Oligonucleotide

<400> SEQUENCE: 15
gcaggcatac actaa                                                          15

<210> SEQ ID NO 16
<211> LENGTH: 187
<212> TYPE: DNA
<213> ORGANISM: Homo sapiens

<400> SEQUENCE: 16
attttccaga aacgtttcga ttataaagat cagcaatttc ttaacttgat ggaaaaattg         60
aatgaaaaca tcaggattgt aagcaccccc tggatccagg taaggccaag ttttttgctt        120
cctgagaaac cacttacagt cttttttttct gggaaatcca aaattctata ttgaccaagc       180
cctgaag                                                                 187

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 17
tccaggggtc ttaacttgat ggaaaaat                                           28

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 18
ggatccaggc ccagaaaaaa agactgt                                            27

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 19
ttcaggggtc ttaacttgat ggaaaaat                                           28

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 20
gaatccaggc ccagaaaaaa agactgt                                            27

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence:Primer
```

-continued

```
<400> SEQUENCE: 21
tccagaaacg tttcg                                                       15

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence:Primer

<400> SEQUENCE: 22
agggcttggt caatat                                                      16

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 23
gcttacaatc ctgatgtt                                                    18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 24
gtaaggccaa gttttttg                                                    18
```